US012263310B2

(12) United States Patent
Jones et al.

(10) Patent No.: US 12,263,310 B2
(45) Date of Patent: Apr. 1, 2025

(54) BILATERAL STIMULATION DEVICES, SYSTEMS, AND RELATED METHODS

(71) Applicants: Stacy Jones, Newton, UT (US); Nephi D. Jones, Newton, UT (US)

(72) Inventors: Stacy Jones, Newton, UT (US); Nephi D. Jones, Newton, UT (US)

(*) Notice: Subject to any disclaimer, the term of this patent is extended or adjusted under 35 U.S.C. 154(b) by 577 days.

(21) Appl. No.: 17/153,700

(22) Filed: Jan. 20, 2021

(65) Prior Publication Data
US 2021/0213239 A1   Jul. 15, 2021

Related U.S. Application Data

(63) Continuation-in-part of application No. PCT/US2019/042802, filed on Jul. 22, 2019.
(Continued)

(51) Int. Cl.
*A61M 21/02* (2006.01)
*A61M 21/00* (2006.01)

(52) U.S. Cl.
CPC ..... *A61M 21/02* (2013.01); *A61M 2021/0016* (2013.01); *A61M 2021/0022* (2013.01);
(Continued)

(58) Field of Classification Search
CPC .......... A61M 21/02; A61M 2021/0016; A61M 2021/0022; A61M 2021/0027; A61M 2021/005; A61M 2205/10; A61M 2205/3303; A61M 2205/3306; A61M 2205/3584; A61M 2205/36; A61M 2205/3606; A61M 2205/42; A61M 2205/502; A61M 2205/581; A61M 2205/8206; A61M 2230/04; A61M 2230/10; A61H 2201/0107; A61H 2201/0134; A61H 2201/1604; A61H 2201/1614; A61H 2201/5005; A61H 23/0254; A61H 23/0245;
(Continued)

(56) References Cited

U.S. PATENT DOCUMENTS 9,408,997 B2    8/2016   Kelley
10,821,261 B2   11/2020  Jones et al.
(Continued)

FOREIGN PATENT DOCUMENTS

DE   202017104857 U1   11/2017
WO   WO 2018/106839 A2   6/2018

OTHER PUBLICATIONS

History of Clinical and Non-Clinical Applications of Bi-Lateral Alternating Stimulation-Tactile (BLAST) Amy Serin, PhD Aug. 6, 2016 (Year: 2016).*
(Continued)

*Primary Examiner* — Sunita Reddy
(74) *Attorney, Agent, or Firm* — Sam Pierce

(57) ABSTRACT

Bilateral stimulation devices, systems and methods are disclosed. In one embodiment, a bilateral stimulation device can include a housing, a tactile stimulator coupled to the housing, a communications module configured to receive wireless communication from a remote device; and a controller module configured to independently and selectively control at least one tactile setting of the tactile stimulator based on wireless communication received from the remote device.

20 Claims, 17 Drawing Sheets

Related U.S. Application Data

(60) Provisional application No. 62/701,323, filed on Jul. 20, 2018.

(52) U.S. Cl.
CPC .......... *A61M 2021/0027* (2013.01); *A61M 2021/005* (2013.01); *A61M 2205/0294* (2013.01); *A61M 2205/10* (2013.01); *A61M 2205/3303* (2013.01); *A61M 2205/3306* (2013.01); *A61M 2205/3584* (2013.01); *A61M 2205/36* (2013.01); *A61M 2205/3606* (2013.01); *A61M 2205/42* (2013.01); *A61M 2205/502* (2013.01); *A61M 2205/581* (2013.01); *A61M 2205/8206* (2013.01); *A61M 2230/04* (2013.01); *A61M 2230/10* (2013.01)

(58) Field of Classification Search
CPC ...... A61H 2201/1207; A61H 2201/165; A61H 2201/501; A61H 2201/5025; A61H 2201/5043; A61H 2201/5048; A61H 2201/5097; A61H 2230/065; A61B 5/0205; A61B 5/4836; A61B 5/165
USPC .................................................... 600/26–28
See application file for complete search history.

(56) References Cited

U.S. PATENT DOCUMENTS

| | | | | |
|---|---|---|---|---|
| 2002/0035995 | A1* | 3/2002 | Schmidt | A61M 21/00 128/898 |
| 2010/0323335 | A1* | 12/2010 | Lee | A61B 5/16 434/236 |
| 2013/0211277 | A1 | 8/2013 | Berg et al. | |
| 2014/0057232 | A1 | 2/2014 | Wetmore et al. | |
| 2014/0179986 | A1 | 6/2014 | Kelley | |
| 2016/0331925 | A1 | 11/2016 | Kelley | |
| 2016/0346501 | A1* | 12/2016 | Hooper | A61B 5/4836 |
| 2017/0014625 | A1 | 1/2017 | Rosenbluth et al. | |
| 2017/0095670 | A1* | 4/2017 | Ghaffari | A61N 1/36139 |
| 2017/0143935 | A1* | 5/2017 | Hanbury | A61M 21/02 |
| 2017/0296429 | A1 | 10/2017 | Mayo et al. | |
| 2017/0296775 | A1 | 10/2017 | Mayo et al. | |
| 2018/0256432 | A1 | 9/2018 | Mayo et al. | |
| 2018/0318545 | A1 | 11/2018 | Jones et al. | |
| 2019/0374742 | A1* | 12/2019 | Hanbury | A61M 21/00 |
| 2020/0147339 | A1 | 5/2020 | Mayo et al. | |
| 2020/0324104 | A1* | 10/2020 | Labuschagne | A61N 5/0622 |

OTHER PUBLICATIONS

Applied Bi-Lateral Alternating Stimulation—Tactile (BLAST) Evidence from Quantitative Electroencephalogram, Amy Serin, PhD Aug. 6, 2016 (Year: 2016).*

Serin, Amy et al. "The Therapeutic Effect of Bilateral Alternating Stimulation Tactile Form Technology On the Stress Response." (2018). (Year: 2018).*

PCT Application No. PCT/US19/42802 Filing date Jul. 22, 2019; Stacy Jones International Search Report, Mailing date Nov. 4, 2019 16 Pages.

* cited by examiner

Rear View

Top View (Cross Section)

BILATERAL STIMULATION DEVICES, SYSTEMS, AND RELATED METHODS

PRIORITY DATA

This application is a continuation-in-part of Patent Cooperation Treaty Application Serial No. PCT/US2019/042802, filed on Jul. 22, 2019, which claims the benefit of U.S. Provisional Patent Application Ser. No. 62/701,323, filed on Jul. 20, 2018, each of which is incorporated herein by reference in their entirety.

BACKGROUND

Bilateral stimulation is a method of treatment that can be used to help a subject process information. For example, bilateral stimulation is often used in a clinical setting to help an individual process traumatic circumstances (i.e. information related to a traumatic event) or anxiety related circumstances as well as general stress reduction and problem solving. The technique involves alternating bilateral visual, auditory, or tactile stimulation in a rhythmic side-to-side pattern. While there are various theories as to how bilateral stimulation works, its positive effects have been confirmed under well-controlled conditions.

DESCRIPTION OF EMBODIMENTS

Figure 1:
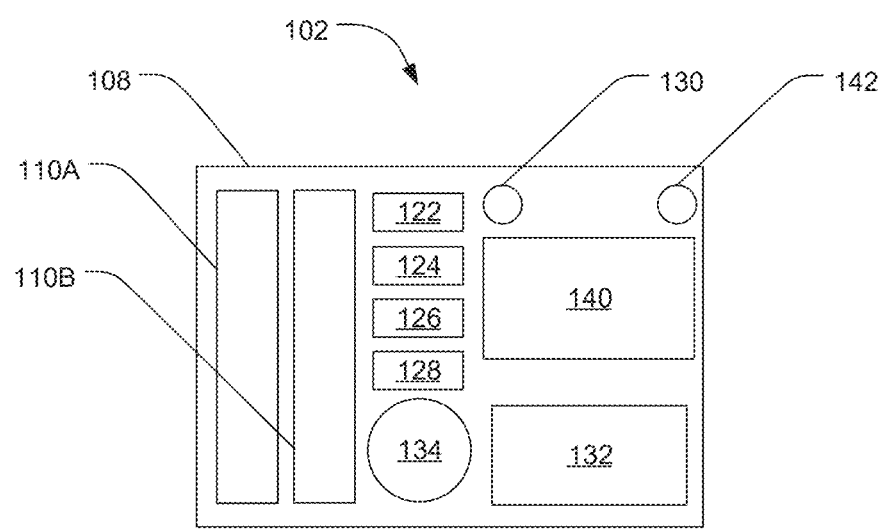
FIG. 1 depicts a bilateral stimulation device, in accordance with some examples of the present disclosure.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a sensor" includes a plurality of such sensors.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

The term "coupled," as used herein, is defined as directly or indirectly connected in an electrical or nonelectrical manner. "Directly coupled" structures or elements are in contact with one another and are attached. Objects described herein as being "adjacent to" each other may be in physical contact with each other, in close proximity to each other, or in the same general region or area as each other, as appropriate for the context in which the phrase is used.

As used herein, "bilateral stimulation" refers to the use of visual, auditory, or tactile external stimuli occurring in a rhythmic side-to-side pattern for the treatment of an adverse health condition.

As used herein, the terms "treat," "treatment," or "treating" refer to administration of bilateral stimulation (BLS) to a subject who is either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "adverse health condition" refers to a structural and/or functional mental or physical abnormality which lowers an individual's quality of life, contributes to a disabling illness, or leads to a premature death. An "adverse health effect" refers to the causation, promotion, facilitation, and/or exacerbation of an adverse health condition. In one example, an adverse health condition can be one or more of: PTSD, social anxiety, separation anxiety, generalized anxiety, panic, depression, relational conflict, phobias, traumatic experiences, chronic-pain induced stress, blended family conflict, marital conflict, relational attachment patterns, spectrum disorders, ADHD, anger management, process addictions, eating disorders, perfectionism, performance anxiety, parenting concerns, academic-focus difficulties, substance abuse, substance addiction, somatic stress, sleep disorders, the like, or combinations thereof.

As used herein, comparative terms such as "increased," "decreased," "better," "worse," "higher," "lower," "enhanced," "maximized," "minimized," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a stimulation process that has an "increased" therapeutic effect or result can refer to improved results or efficacy attained by the process as compared to a similar or different process intended for treatment of the same condition or experience.

As used herein, the term "tactile stimulator" refers to a component, device, or system which is capable of providing tactile sensory input to a subject via stimulation of the subject's tactile receptors, including without limitation, mechanoreceptors, thermoreceptors (e.g. sense of heat and cold), nociceptors (e.g. pain receptors), photo receptors, and chemoreceptors. Examples of mechanoreceptors include without limitation lamellar corpuscles (Pacinian corpuscles), tactile corpuscles (Meissner's corpuscles), Merkel nerve endings, and bulbous corpuscles (Ruffini corpuscle). Additionally, "tactile stimulation" refers to receipt by a subject of stimulation through the use of a tactile stimulator.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EXAMPLE EMBODIMENTS

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

Eye movement desensitization and reprocessing (EMDR) is a standard method for treating post-traumatic stress disorder (PTSD) and has been recommended by the American Psychiatric Association. The technique typically involves a unique procedure in which a therapist exposes a patient to bilateral stimulation (BLS). In further detail, BLS typically involves a rhythmic pattern of stimuli that alternate from side-to-side. The stimuli can include visual stimuli, auditory stimuli, or tactile stimuli.

While BLS can be very effective in the clinic to treat PTSD and other stress-related or trauma-related emotional conditions, BLS can also provide a number of positive effects that can be beneficial on a more routine basis in response to general stressors. As a whole, stress in the general public is on the rise and there is an ever-increasing need for resources to help alleviate stress, including resources that are non-invasive and do not include medication. In addition, a large proportion of the general population (e.g. young children, infants) have limited options available in terms of resources for aiding in the reduction of stress given that most current treatments for stress reduction are not age appropriate for them (i.e. traditional talk therapy, use of psychotropic medications, etc.). High levels of stress have a negative impact on many aspects of functioning and wellbeing, including decreases in productivity in academic and employment settings, relationship quality, ability to manage general life stressors, levels of adaptability, resiliency factors, and overall physical health, for example.

The mind-body connection is also highly documented in that high levels of stress reap havoc on body systems, just as physical pain and ailment enhance levels of stress. With this in mind, certain vibrational frequencies can be associated with enhanced physical states and wellbeing. Further, these vibrational frequencies can aid in the healing process of several body systems.

Accordingly, devices, systems, and methods are disclosed herein to help decrease overall stress levels and enhance relaxation effects, thus potentially decreasing the incidence and extensity of co-morbid factors associated with high stress states, including but not limited to negative mood states, difficulties with sleep, decreased productivity, physical ailments, and other co-morbid symptoms. Such devices, systems, and methods are unique in that they can combine the proven mental processing and relaxation attributes of BLS with one or more specific complimentary external stimuli and/or cues that enhance the end user's desire to avoid states of stress (panic/anxiety, sleeplessness, mentally overwhelmed, or pain) and instead achieve a more ideal and desired physical and emotional state of wellbeing (for example the feeling of calm, clarity, enhanced problem solving abilities, relaxation, sleepiness and/or restfulness, and physical healing, and the potential for enhanced brain resiliency) by using these devices and selecting pre-configured default parameters tailored to address particular types of stress and processing modes. As will be described in greater detail below, embodiments of these devices, systems, and methods can also include biofeedback features for the purpose of actively re-syncing both breathing pattern and heart rate to the desired state of individual wellbeing (stress reduction). Devices can also include features that utilize different frequencies known to aid in healing in various body systems.

More specifically, the present disclosure describes a number of devices, systems, and methods useful in and/or employing BLS to induce a natural state of relaxation and calm to help deal with a number of stress-related triggers and situations.

As a further note, in the present disclosure, when discussing the various devices, systems, and methods, each of these discussions can be considered applicable to each of these examples, whether or not they are explicitly discussed in the context of that example. Thus, for example, in discussing details about the BLS devices per se, such discussion also refers to the BLS systems and methods, and vice versa.

In some embodiments, BLS devices can include a housing and a variety of electronic components associated therewith. As will be discussed in further detail below with respect to the BLS system, the BLS devices can employ a number of configurations to facilitate modular BLS systems. Thus, none of the various BLS device features described herein are to be interpreted as being required, but as optional components for a particular embodiment of a BLS device.

With this in mind, the housing of the BLS devices can include any suitable housing to accommodate and protect the tactile stimulator and/or other electronic components associated with the BLS devices. Further, the materials used to manufacture the housing are not particularly limited. However, it is noted that, in some examples, the housing can be associated with a fabric material. In such examples, it may be desirable for the housing to comprise a material that is sufficiently thermally insulating to minimize fire hazards. Further, in some examples, the housing design may include features that encapsulate the majority of the device components using an insulating material (e.g. urethane foam, low density olefin, the like, or a combination thereof) as this can reduce the detectability of audible vibrations to those nearby the device. In some additional examples, the portion of the device that is placed directly or indirectly against the end user can be formed or fabricated of a more rigid material so as to improve conduction of a tactile signal to the intended recipient.

In some examples, a tactile stimulator can be coupled to the housing. The tactile stimulator can include any device for producing a tactile stimulation at a desired vibrational frequency when the tactile stimulation is vibrational stimulation. In some examples, the tactile stimulator can include a piezoelectric device, an electromechanical actuator, an electromagnetic device, a disc vibration motor, an ultrasonic vibrator (e.g. a vibrator that generates low resonance frequency, resonance, standing wave form, or the like to produce vibrational stimuli), the like, or a combination thereof.

In some examples, an electromechanical actuator can comprise an electrical motor. In one example, the electrical motor can include an unbalanced shaft or a balanced shaft. When the electrical motor includes an unbalanced shaft, the electrical motor can be multiphase stimulation generators which can be driven with armature speed to generate multiphase frequencies (which can be perceived as vibrations). When the electrical motor includes a balanced shaft or an unbalanced shaft, the electrical motor can be a shaft mass motor driven with armature acceleration to generate increased inertia based on single phase stimulation (which can be perceived as touch). Both approaches can include alternatives such as servo or brushless motor designs that can provide increased precisions, longevity, dynamic range, efficiency, or the like.

In one example, devices can include any device for producing a tactile stimulation to provide a desired therapeutic effect. The tactile stimulation type can include one or more of vibration, linear, tap, resonance, touch, electro-stimulation, heat, cold, ultrasonic patterns, the like, or combinations thereof. In one example, a subject having a negative response to a stimulation type (e.g., vibration) can have a positive response to a distinct stimulation type (e.g., tapping). In another example, a subject having a negative response to an ultrasonic pattern can have a positive response to a temperature-based stimulation type (e.g. hot or cold).

In another example, the tactile stimulation type can be used in combination or synchronized in time with another tactile stimulation type. In one example, a tactile stimulation type such as vibration can be combined or synchronized in time with a temperature-based tactile stimulation type, such as hot or cold. In another example, a tactile stimulation type such as resonance can be combined or synchronized in time with electro-stimulation. In another example, a tactile stimulation type such as ultrasonic can be combined or synchronized in time with a temperature-based tactile stimulation type, such as hot or cold. The tactile stimulation types can be combined in any suitable manner to provide a therapeutic effect.

The tactile stimulators can be configured to operate according to a tactile program (e.g., a vibration program) which is a component of a BLS program, and vibrate at a variety of vibrational frequency ranges when the tactile program is a vibrational program. For example, the tactile stimulators can be configured or programmed to vibrate at a vibrational frequency of from about 5 hertz (Hz) to about 400 Hz. In some further examples, the tactile stimulators can be configured or programmed to vibrate at a vibrational frequency of from about 20 Hz to about 100 Hz. In additional examples, the tactile stimulators can be configured or programmed to vibrate at a vibrational frequency of from about 20 Hz to about 75 Hz. In still additional examples, the tactile stimulators can be configured or programmed to vibrate at a vibrational frequency of from about 75 Hz to about 95 Hz.

It is noted that frequencies between 5-100 Hz can provide physical benefits in a number of areas, including enhancing bone density, enhancing muscle repair, decreasing breathing difficulties, enhancing heart health, and enhancing a sense of relaxation. Further, bilateral stimulations can enhance cognitive abilities, such as an ability to think and organize thought, processing memories and information, and activate aspects of the brain to decrease stress and enhance overall performance (e.g. can switch off parasympathetic nervous symptom and sympathetic nervous symptom). The disclosed BLS devices uniquely combine both approaches, hence enhancing overall health and well-being across a greater range of factors.

In some examples, a plurality of tactile stimulators can be coupled to a common housing. Where this is the case, one or more tactile stimulators can be configured or programed to vibrate at the same or different frequencies. In some cases, the frequency at which the tactile stimulator(s) is/are configured to vibrate can be based on a particular condition to be treated or ameliorated. For example, in some cases, it can be desirable to use vibrational frequencies of from about 20 Hz to about 75 Hz to treat physical conditions or symptoms, whereas it can be desirable to use vibrational frequencies of from about 75 Hz to about 95 Hz to treat emotional conditions or symptoms. Thus, in some cases, a first tactile stimulator can be configured or programmed to vibrate at a first frequency (e.g. from about 20 to about 75 Hz) and a second tactile stimulator can be configured or programmed to vibrate at a second frequency (e.g. from about 75 to about 95 Hz). As such, in some examples, the BLS devices can be configured to treat both physical and emotional conditions and/or symptoms. In other examples, the first tactile stimulator and the second tactile stimulator can both be configured to vibrate within a common vibrational range or at the same vibrational frequency.

Regardless of the vibrational frequency or frequencies generated, some examples of the present BLS devices are intended to be suitable for use in routine settings. However, some routine settings in which it can be desirable to use the BLS devices described herein can also be formal settings, quiet settings, or other settings where it would be otherwise undesirable for a BLS device to be audibly noticed by others. As such, in some examples, the tactile stimulators can also be configured to maintain a decibel level that is minimally disruptive or noticeable to others. For example, in some cases, the tactile stimulators can be configured to have a decibel level at or below 35 decibels at a distance of 0.5 meters (m) or less from the tactile stimulator. In some additional examples the tactile stimulators can be configured to have a decibel level at or below 30 decibels at a distance of 0.5 m or less from the tactile stimulator. In other examples, the tactile stimulators can be configured to have a decibel level at or below 25 decibels at a distance of 0.5 m or less from the tactile stimulator. In still other examples, the tactile stimulators can be configured to have a decibel level of from about 25 decibels to about decibels at a distance of 0.5 m or less from the tactile stimulators.

The decibel level can be maintained at a desired level in a number of ways. In some examples, the tactile stimulators themselves can be configured to have the desired decibel level. In other examples, as described above, the housing can be configured to dampen or control the decibel level of the tactile stimulators. In still other examples, other sound dampeners can be employed in the BLS devices to dampen or control the decibel level of the tactile stimulators. For example, in some cases, design features can be employed to specifically hold the device tightly against the skin or clothing of the end user to provide one or more benefits. In some specific examples, a tight fit can provide better tactile signal transmission to the target area of the end user. In some additional examples, a tight fit can dampen external vibrations that are the most common or predominate source of vibrations responsible for any undesirable audible noise that is distracting to others nearby.

While it can be valuable to maintain a relatively low decibel level, it can also be important to maintain sufficient vibrational intensity to provide an effective treatment or benefit. For example, if the vibrational intensity is too low, the tactile stimulus may be too weak to be therapeutically effective. However, if the vibrational intensity is too strong, the stimulus may be overbearing, distracting, loud, etc., which can also decrease the therapeutic benefit of the stimulus. Further, vibrational intensity can be related to a level of stress as well as individual differences and preferences for sensorimotor experiences. For instance, some people under high stress may experience somewhat dissociative symptoms (e.g. feeling of being disconnected from body, feeling numb or "out of it,") and may benefit from a higher level of vibrational intensity to be effective. Others may feel over sensitive to the vibrations due to a number of factors (e.g. age, history of traumatic experiences, general preferences, etc.) and would thus prefer a less intense tactile stimulus.

Vibrational intensity can be measured in a number of ways. For example, vibrational intensity can be quantified in terms of displacement (amplitude), which is typically measured at the location of maximum displacement relative to stationary (natural) position. In the SI system, the amplitude is measured in units of meters (m). While the intensity of a vibration depends upon amplitude, it is also affected by acceleration or how quickly speed changes over time and this is expressed in units of meters per second (m/s^2), whereas the speed of vibration is measured in units of meter (m/s).

Additionally, the International Standards Organization (ISO) has established root mean square (RMS) as the standard for measuring amplitude. More specifically, the RMS value of a pure sinusoid is equal to the area under half the wave form and this corresponds to RMS=0.707× peak on a pure sinusoid. However, pure sinusoids are rarely found in measuring mechanical vibrations and this designation is helpful in making point of comparisons more accurate.

Another physical phenomenon of value for this type of product design is resonance, because every object tends to vibrate at one particular frequency called the natural frequency. The natural frequency is influenced by the object's physical features of mass, size, shape, and composition. When a machine vibrates at its resonance frequency it transfers the maximum amount of energy to the receiving object. To this end, the features of intensity, acceleration, and resonance are important parameters when designing a tactile stimulator. The design of the present BLS devices can be optimized to produce a soothing and discernable stimulus that also operates reliably while consumes relatively low power and producing low level of undesirable noise.

The tactile stimulators and/or other device components can generally be controlled by a controller module. For example, the controller module can be configured to execute stored tactile programs using the tactile stimulator(s). For example, in some cases, the controller module can be pre-programmed to have specific default tactile settings (e.g., vibrational settings) based on a number of pre-determined treatment modalities. For example, as described above, the BLS devices can be used to treat physical and/or emotional conditions or symptoms. With this in mind, the controller module can be pre-programmed to have specific default tactile settings (e.g., vibrational settings). In other examples, the BLS devices can include user controls configured to allow user customization of tactile settings (e.g., vibrational settings).

Broadly, the stored tactile programs typically include a tactile pulse followed by a tactile pause. However, for some treatment modalities, a sustained or prolonged tactile pulse can also be employed, as will be described in further detail below. With respect to the tactile pulses followed by a tactile pause, the tactile pulse can typically have a duration of from about 0.05 seconds to about 5.0 seconds, or from about 0.1 seconds to about 2.0 seconds. In some other examples, the tactile pulse can have a duration of from about 0.6 seconds to about 1.0 seconds, about 0.7 seconds to about 0.9 seconds, or about 0.8 seconds. In still other examples, the tactile pulse can be from about 0.05 seconds to about 0.5 seconds, from about 0.1 seconds to about 1 second, from about 0.5 seconds to about 1.5 seconds, from about 1 second to about 2 seconds, from about 1.5 seconds to about 3.5 seconds, or from about 2 seconds to about 5 seconds. The subsequent tactile pause can typically have a duration of from about 0.1 seconds to about 2.0 seconds. In some other examples, the tactile pause can be from about 1.0 seconds to about 1.4 seconds, about 1.1 seconds to about 1.3 seconds, or about 1.2 seconds. In some specific examples, the tactile pause can be longer in duration than the tactile pulse.

In some examples, it can be desirable to have an interim pause after a number of pulse/pause cycles. The interim pause can be valuable to help calm the brain and refocus thought during the treatment period. In some examples, an interim pause can be programmed into the tactile program to occur at a rate of from about every 15 to about 45 pulse/pause cycles, or from about every 20 to about 40 pulse/pause cycles. In some additional examples, it can be desirable to perform an interim pause at various points during the treatment period, whether or not pulse/pause cycles are employed. For example, the interim pause can occur at a rate of from about every 20 seconds to every 120 seconds, every 30 seconds to every 90 seconds, every 45 seconds to every 75 seconds, or about every 60 seconds. In some other examples, the interim pause can be performed at least once, at least twice, at least three times, four times, five times, or more during the treatment period. The interim pause itself can typically have a duration of from about 5 seconds to about 5 minutes. In some specific examples, the interim pause can have a duration of from about 5 to about 10 seconds, about 6 to about 8 seconds, or about 7 seconds. In some additional examples, the interim pause can have a duration of from about 10 seconds to about 60 seconds, from about 30 seconds to about 90 seconds, from about 60 seconds to about 120 seconds, from about 90 seconds to about 180 seconds, from about 120 seconds to about 240 seconds, or from about 180 seconds to about 300 seconds. An interim pause can provide a framework for focused deep breathing, thus enhancing overall stress management, and can aid in problem solving by helping to provide structure and organization to thoughts (similar to the period at the end of the sentence), etc.

The treatment period can also be programmed into the tactile program. The treatment period can generally be a period of from about 5 to about 120 minutes. In some specific examples, the treatment period can be about 5 minutes, about 10 minutes, about 15 minutes, about 20 minutes, about 25 minutes, about 30 minutes. In additional examples, the treatment period can be about 45 minutes, about 60 minutes, about 75 minutes, about 90 minutes, about 105 minutes, or about 120 minutes. In some further examples, the treatment period can be from about 5 minutes to about 10 minutes, from about 10 minutes to about 15 minutes, from about 15 minutes to about 20 minutes, from about 20 minutes to about 25 minutes, or from about 25 minutes to about 30 minutes. In still additional examples, the treatment period can be from about 30 minutes to about 45 minutes, about 45 minutes to about 60 minutes, about 60 minutes to about 75 minutes, about 75 minutes to about 90 minutes, about 90 minutes to about 105 minutes, or about 105 minutes to about 120 minutes. For example, a timer can be associated with the controller module to terminate the treatment period at the expiration of a predetermined time limit. More specifically, after the treatment period concludes, the controller module can operate to turn the BLS device off or at least cause tactile stimulation to stop.

In some further examples, the controller module of the BLS devices or systems can employ an intensity fade as a sleep function. In further detail, the controller module can be equipped with program logic to execute a diminishing intensity fade over a desired period of time. As one non-limiting example, the controller module can employ a sleep function to linearly diminish the intensity of the tactile pulses over the last 10% to 100%, 5% to 50%, or 3% to 30% of the treatment period. Of course, non-linear intensity fades can also be used, as desirable. Further, the specific duration of the intensity fade can also be adjusted, as desirable. In some specific examples, when the sleep function is enabled, the last 1 minute to 30 minutes (e.g. the last 30 minutes, 20 minutes, 10 minutes, 5 minutes, 3 minutes, 2 minutes, etc.) of the treatment period can execute a linear (or non-linear) fade sequence such that the intensity diminishes (ramps down) linearly from 100% of an operating intensity level and is reduced progressively down to 10% of the operating intensity level before automatically turning off the BLS device. In some cases, 20% of the operating intensity level can be the upper signal threshold level that most end users can easily discern.

In some additional examples, the BLS device can be configured to operate based on the specific instructions provided by a remote device. Thus, in some examples, the BLS device may not operate entirely on a set or preprogrammed tactile program. Rather, the BLS device can be controlled by a remote device to perform a user defined program, a software selected/adjusted program, the like, or a combination thereof based on instructions provided by the software programming. In some cases, the software programming can include artificial intelligence (AI) programming to adjust tactile programs in real time.

In some examples, a controller or controller module can be controlled by a user or subject via a remote device, via a physically connected device (e.g. through wires, cables, or the like), via a display and/or switch associated with the housing, the like, or a combination thereof. Where the controller module is controlled via a remote device, the BLS devices can further include a communications module or component (e.g. communications interface) that is configured to receive instructions from a remote device and communicate those instructions to the controller module to control the tactile stimulator accordingly. The communications module can be configured to communicate with the remote device via any suitable wireless protocol. Non-limiting examples can include Bluetooth® (e.g. Bluetooth® low energy (LE)), Zigbee, other suitable IEEE protocols, WiFi, WiMAX®, the like, or other suitable wireless protocols.

In some further examples, the BLS devices can include a power module or source configured to power the BLS devices. Any power source sufficient to adequately power the BLS devices may be used. For example, batteries, capacitors, and/or other power sources may be used. In one aspect, the power module can include a battery. In one example the battery can be a rechargeable battery. Other components can be included in the power module, such as wires and electrical connections required to operably connect the battery to other modules within the BLS devices that require power for their operation. In one specific example, the power module may include components that inductively charge the battery when exposed to an adequate external influence, such as a wireless or magnetic influence. In such embodiments, if charging of the battery is necessary or desired, the proper external influence can be brought within a sufficient range to operate the inductive components and charge the battery without physically accessing the BLS device. In other examples, charging of the battery can be performed via physical connection to a charging source. In yet other examples, power module can include disposable batteries. In some specific examples, the BLS devices can include an on/off switch to engage the power module of the BLS devices. In some additional examples, the power module of the BLS devices can be activated remotely. In additional examples, the lifetime of the battery can be extended by adapting to a routine of an end user. For example, the battery can be prevented from fully charging before a user is expected to use the BLS device.

In some examples, the BLS devices can further include a speaker for generating an auditory bilateral stimulus, for providing instructions (e.g. for breathing, for isometric exercises, etc.), or for generating other desirable auditory stimulus. The controller module can be further configured to control operation of the speaker. In some further examples, the BLS devices can include a data module or store (e.g. a memory component) for collecting and/or storing audio data for playback via the speaker. For example, in some cases the data module can be preprogrammed with specific audio files that can be played back via the speaker to generate an auditory bilateral stimulus. In some specific examples, the auditory bilateral stimulus can be or simulate a cat's purr, or the like. In some specific examples, the auditory stimulus can be configured to have a frequency that matches the stimulus of a tactile stimulus. In other examples, the auditory stimulus can be configured to have a frequency that is distinct from a tactile stimulus. For example, in some cases the auditory stimulus can have a frequency in the range of from about 20 Hz to about 75 Hz, whereas the vibrational frequency can be from about 75 Hz to about 95 Hz, or vice versa, for example. In additional examples, the data module may be configured with audio files of classical music, sounds from nature, and/or other generally soothing sounds. In still other examples, the data module can be associated with a microphone to allow an end user to record audio for playback (e.g. a caregiver singing a lullaby, a caregiver reading a story, etc.). Alternatively, the audio file can be recorded on a remote device and transferred to the data module via the communications module.

In still other examples, the BLS devices (or BLS systems) can include a receptacle for a fragrance. Non-limiting examples can include a pocket or pouch, a sponge, an absorbent cloth, and/or other absorbent material suitable for holding and releasing a fragrance (e.g. an essential oil, a fragrance associated with a loved one, etc.). In some examples, the receptacle can include a pocket, pouch, or the like directly associated with the BLS devices (or BLS systems) for securing a suitable fragrant material (e.g. a sponge, absorbent cloth, a piece of cloth previously worn by a caregiver, etc.) to the housing. In other examples, the receptacle can be coupled to the housing via other suitable coupling features, such as a snap, a hook and loop fastener, a clip, a clamp, a magnet, an adhesive, the like, or a combination thereof. In the case of a BLS system, as will be described in further detail below, the receptacle for a fragrance may be directly associated with one or more flexible materials or articles of the system, whether or not the associated BLS device includes a separate receptacle for a fragrance.

In another example, the BLS devices can include a transponder configured to provide location data for the BLS device. For example, an end-user can locate a lost BLS device via a software interface for the BLS device.

In additional examples, the BLS devices can include one or more biofeedback sensors, such as a heart rate sensor or other suitable sensor, for monitoring heart rate, breathing, etc. In some examples, the biofeedback sensor can be configured to transmit and/or store data in the data module and/or transmit data to a remote device (e.g. a smart device, computer, server, or the like). In some additional examples, the controller module can be equipped with program logic or circuitry that is configured to control the operation of the tactile stimulators based on the data collected by the biofeedback sensor. In still additional examples, the controller module can be equipped with program logic that is configured to play back audible tones, audible instructions, visual cues, or the like to help the user regulate his or her breathing and/or heart rate based on the data collected by the biofeedback sensor. These biofeedback programs, or other suitable biofeedback programs, can be executed alone or together, as desired, to help regulate the breathing and/or heart rate of an intended user.

Biofeedback devices (i.e. BLS devices including biofeedback sensors and associated biofeedback stimuli) can help teach self-regulation of brain waves, heart rate and/or breathing to achieve certain brain waves/states, coherence in heart rate, and breathing to maximize the relaxation effect of the treatment. For example, bilateral biofeedback devices can aid to release tension and stress as well as enhance problem solving strategies. In further detail, biofeedback can enhance the bilateral stimulation effect and the bilateral stimulation effect can enhance the biofeedback. For example, enhanced relaxation can be achieved when engaging in problem solving and processing of information (this can help to further resolve emotional and cognitive difficulties and stresses). Additionally, enhanced ability to resolve specific anxiety, frustration, and stresses associated with specific situations that increase irregular heart rate can be achieved, thus enhancing overall self-regulating abilities. As such, bilateral biofeedback devices can be used to address a wide range of emotional and physical conditions. Further, BLS devices can incorporate features to measure and provide instruction to enhance breathing patterns and engagement in specific brainwaves to enhance the idealized calm state of the end user.

Figure 15:
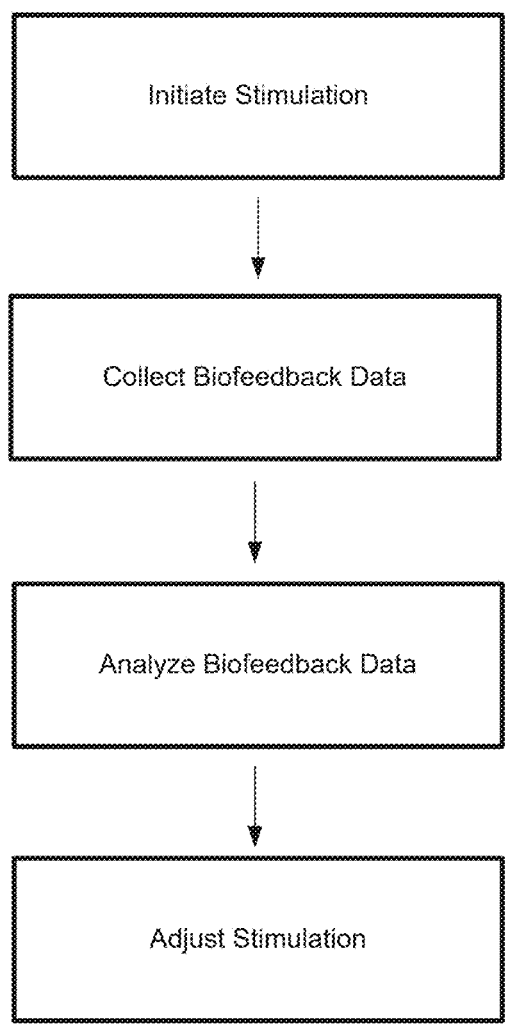
FIG. 15 is a flow diagram showing a process for automated control of a device or system in providing treatment in a way that is self-adjusting.

For example, the biofeedback device features and associated algorithms can employ various levels of software programming. Referring to FIG. 15, at a basic level, once a specific BLS program has been selected and applied to a subject/patient, biofeedback information can be collected and analyzed during treatment and the BLS program altered as needed in order to generate biofeedback that more closely matches and expected result or outcome.

More advanced features can also include artificial intelligence (AI) wherein the software programmed into the devices is able to transact multiple inputs/outputs (on-board) and is able to use these and other internal data in combination with external variables (off-board from separate devices via wireless communication). Variables can include those that are specific to human physiology, human emotion, and human thought patterns. Potential benefits of these more complex algorithms can include either direct or passive interaction with the end user. Thus, the devices can thereby effectively learn about the end user in order to tailor the experience specifically to the individual's needs for the intent to improve the experience or outcome of the therapeutic benefits delivered (thus improving over time the effectiveness of the devices and thereby improving the effectiveness and capacity of a specific device or a large population of related devices).

These improvements can be realized by the AI or software program either by following a predefined program or by a process of trial and error whereby the response is measured, processed, and rationalized by the program (all this information can be archived internally via the data storage module and/or communicated to (e.g. unidirectional communication) or with (e.g. bi-directional communication) to a remote device (e.g. a smart device, computer, server, etc.) via the communications module. This data can be retained for comparison later, metadata analysis, or for real-time comparative assessment to see how the end user responds to stimuli and how new stimuli produced by the devices are received by the end user; all for the purpose of continuous improvement of the devices, overall performance benchmark analysis, or for improving the design of a particular device or designing new devices for alternative applications.

One non-limiting example of a BLS device 102 is illustrated in FIG. 1. In further detail, the BLS device 102 includes a housing 108. A first tactile stimulator 110A and a second tactile stimulator 110B are coupled to the housing. A controller module 122 is configured to control operation of the tactile stimulators 110A, 110B and execute stored tactile programs using the tactile stimulators 110A, 110B. A communications module 124 is configured to receive instructions from a remote device, as described above. A power module 126 is configured to power the various electrical components of the BLS device 100. A data or memory module 128 is configured with audio files for audio playback via the speaker 130. A display 140 can indicate status of the tactile programs, selected/pre-programmed settings, etc. and the various settings can be adjusted by the user via one or more switches 142. A fragrance receptacle 132 can include a pouch, sponge, absorbent cloth, other absorbent material, the like, or a combination thereof for providing a desirable or soothing fragrance. A biofeedback sensor 134 can collect physiological data, which can be used to control operation of the device, trigger a biofeedback stimulus, the like, or a combination thereof. Of course, FIG. 1, and other figures associated with this disclosure, are merely illustrative examples depicted for discussion purposes and are not intended to be interpreted as requiring the specific design, configuration, or layout as depicted. Also, the figures associated with this disclosure are not necessarily drawn to scale and are not intended to be interpreted as such.

One or more BLS devices can be synchronized or otherwise paired with one or more other BLS devices to form a BLS system. With this in mind, BLS devices can take many forms to provide a wide variety of BLS systems. For example, in some cases, the BLS systems can be modular, allowing for mixing and matching of various BLS devices to achieve a variety of desired treatment modalities. In other examples, the BLS systems are not modular.

It is noted that the various BLS devices can be synched or otherwise paired to one another in a number of ways to form or provide a BLS system. For example, in some cases, the BLS devices can be synched via a common control unit, which can be wirelessly connected to the BLS devices or connected to the various BLS devices via wires or other suitable physical connection. Various control units can be employed. For example, in some cases, the control unit can be a remote device equipped with an executable program (e.g. an app) to control the various BLS devices. In other examples, the control unit can be specifically tailored to control the various BLS devices (i.e. the control unit does not have any intended alternative functionality). Other suitable control units can also be employed, including combinations of suitable control units. In other examples, individual BLS devices can be equipped to control other BLS devices (e.g. one BLS device can be designated as the controller and the other BLS device(s) can act as slave to the designated controller). Other suitable configurations can also be used. Whatever the case, the control unit or designated controlling BLS device can be equipped with all necessary communications modules, control modules, power modules, data modules, and/or other electrical hardware and/or software necessary to control and synchronize the BLS devices of the BLS system. Similarly, depending on how the BLS system is configured, individual BLS devices may require more or less hardware/software to provide the intended functionality.

In further detail, BLS systems typically include a plurality of BLS devices coupled to one or more flexible articles. In some examples, the BLS devices can be removably coupled to the one or more flexible articles to facilitate a modular BLS system. In other examples, BLS devices can be permanently coupled (i.e. not intended to be removable) to the one or more flexible articles.

A variety of flexible and/or wearable articles can be employed in the BLS systems. Non-limiting examples can include a belt, a bra, a tank top, a shirt, a bracelet, a wristband, a compression sleeve, a compression cuff, a sock, a slipper, a sandal, a shoe, pajamas, a onesie, a smock (e.g. a Snuggie™), a robe, earphones, a blanket, a weighted blanket, a pillow, a mattress, a stuffed animal, a shoulder wrap, a joint brace or wrap, a wound wrap, the like, or a combination thereof. In some examples, the flexible article can include a flexible cover or case (e.g. pillow case, laptop carrying case, a book cover, etc.) that is designed to fit over an otherwise generic article or device. In some specific examples, the flexible articles can include one or more pockets, pouches, snaps, clips, clamps, magnets, hook and loop fasteners, zippers, the like, or combinations thereof for removably coupling one or more BLS devices thereto. In one specific example, the flexible article can be a compression sleeve for use on the human body (e.g. limbs and/or joints) combined with bilateral stimulation integrated into the sleeve to include a conducting element for spreading tactile stimuli through an enhanced or augmented surface area. Conducting elements can similarly be used in other flexible articles and can include any suitable material, structure, etc. to propagate, or increase the surface area of, the tactile stimuli.

In some further examples, a number of different article types can be used in a common BLS system. For example, a first article type (e.g. one or more wristbands) can include one or more BLS devices. The BLS devices in one or more first flexible article types can be further synched to BLS devices in one or more additional flexible articles (e.g. one or more second flexible article types, one or more third flexible article type, etc.), such as socks, a pillow, earbuds, etc. In some examples, this can be accomplished by synching individual BLS devices across all article types. In other examples, this can be accomplished by synching individual control units for each article type, each control unit being configured to control one or more BLS devices. In either case, syncing can be performed via wired connection or via wireless connection.

In some examples, a BLS device can be coupled or synchronized with a smart watch, a smart phone, or other device to form a BLS system. In some examples, the BLS device and synchronized smart device can be controlled via a remote device to provide bilateral stimulations to a subject. In other examples, the BLS device and smart device can be connected via wired connections.

In some examples, the BLS system can further include a microphone for receiving audio communications from an end user. For example, in some cases, the BLS system can employ software programming including biofeedback features and/or artificial intelligence (AI) programming that can prompt the user to provide audio responses to questions. The microphone can detect the audio responses and transmit the responses to a remote device or controller module to adjust one or more parameters of the BLS system or an individual BLS device, for example.

In some additional examples, the BLS system can further include a visual device to provide a visual cue, a virtual augmented reality effect, the like, or a combination thereof. The visual device can include a display, glasses, a head set, or the like. The visual device can be connected (e.g. wired or wireless) to one or more other devices of the BLS system. In some examples, the visual device can be configured to provide visual cues, instructions, questions, images, the like, or a combination thereof, that can be synched with one or more BLS system devices or programs. In one example, the question can be a communication that can elicit a response or feedback from a user. For example, the question can be an interaction with an icon, a graphic, an image, a word, a phrase, an infographic, a situation, a story, a tone, a color, a shape, a diagram, an animation, an audio clip, a video display, or the like.

A number of BLS system configurations can be desirable, some of which will be described below. However, the specific configurations described herein are not intended to be limiting, as other desirable configurations will be apparent to one skilled in the art based on the present disclosure.

Figure 2A:
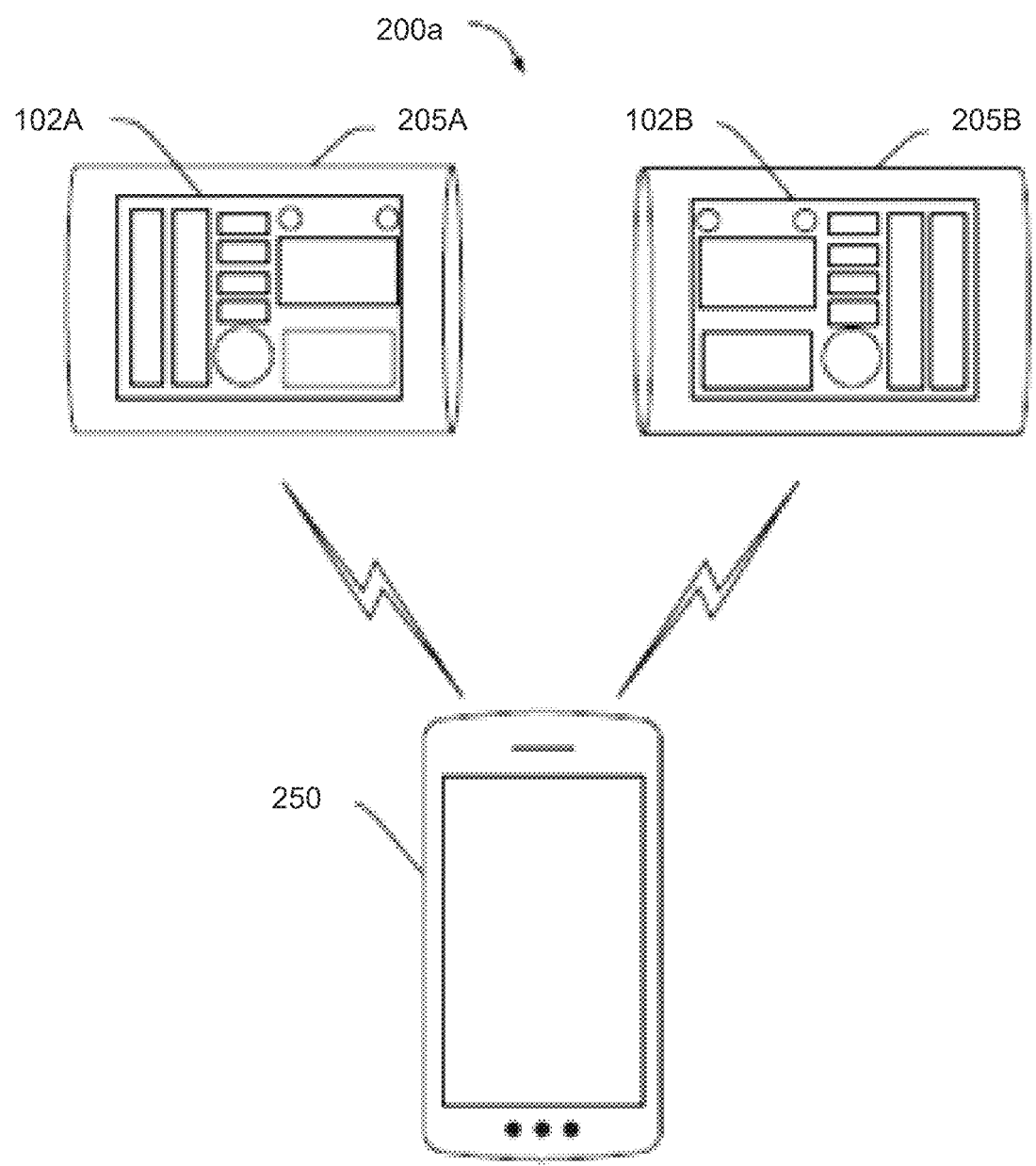
FIG. 2a depicts a bilateral stimulation system associated with individual wristbands, in accordance with some examples of the present disclosure.

One non-limiting example of a BLS system 200a is illustrated in FIG. 2a. In this particular example, individual BLS devices 102A, 102B (each being equivalent to the BLS device 102 illustrated in FIG. 1) are coupled to flexible articles (e.g. wristbands) 205A, 205B. In this particular example, operation of the BLS devices 102A, 102B can be controlled wirelessly via a remote device 250 (e.g. a smart phone, tablet, computer, router, etc.). In other examples, individual BLS devices can be connected to a control unit via wired connections. Remote access to the BLD devices 102A, 102B can be granted to a non-user with control of the remote device 250.

Figure 2B:
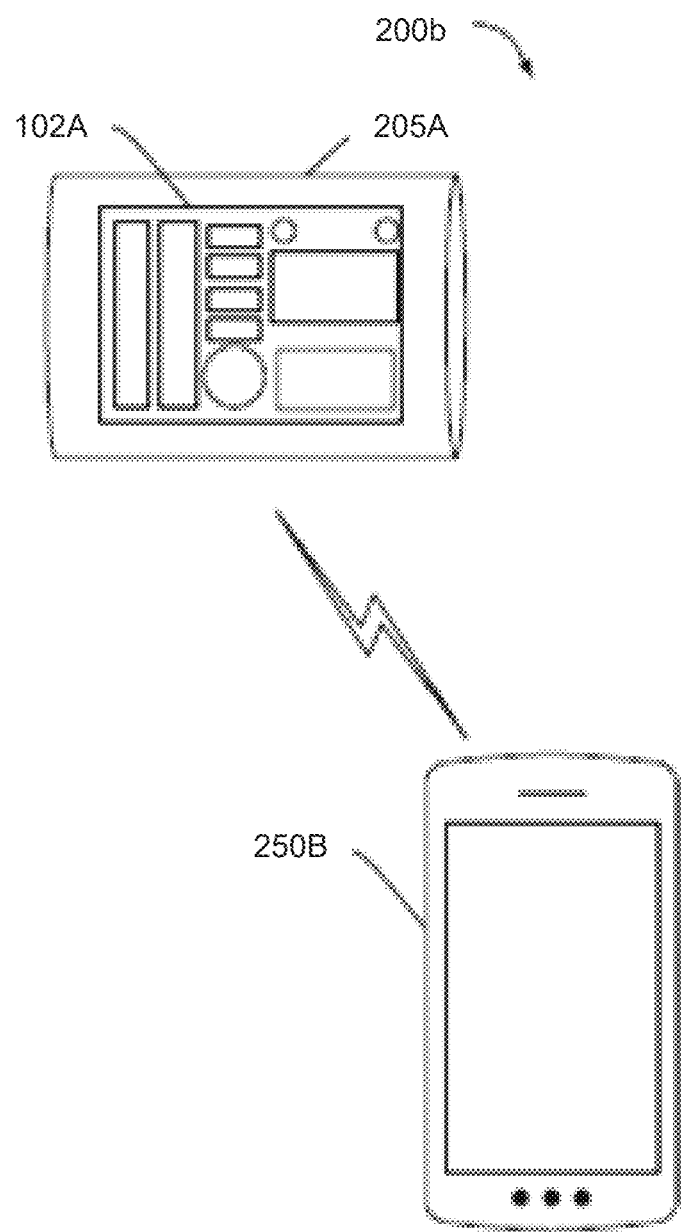
FIG. 2b depicts a bilateral stimulation system with one BLS device, in accordance with some examples of the present disclosure.

Another non-limiting example of a BLS system 200b is illustrated in FIG. 2B. In this particular example, an individual BLS device 102A, which can couple to a flexible article 205A, can be controlled either wirelessly or with a wired connection via a remote device 250B (e.g. a smart phone, tablet, computer, router, or the like). In this example, the remote device 250B can be a smart device that operates as an additional BLS device (e.g., provide tactile stimulus pulses) and as a display that can indicate the status of the tactile programs, selected/pre-programmed settings, or the like, and the various settings can be adjusted by the user.

Figure 2C:
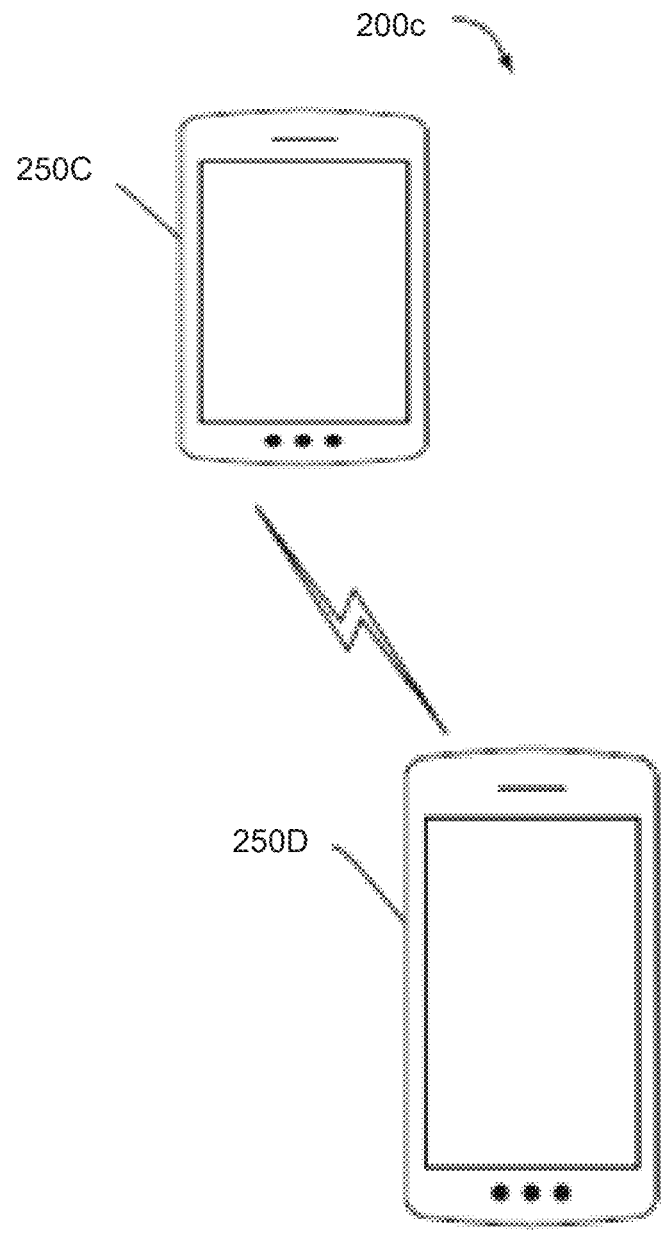
FIG. 2c depicts a bilateral stimulation system in accordance with some examples of the present disclosure.

In another non-limiting example, a BLS system 200c, as illustrated in FIG. 2C can comprise a first smart device 250C and a second smart device 250D. The first smart device 250C, second smart device 250D, or both smart devices 250C and 250D can operate as a common control unit that can include a power module, control module, communications module, data module, and other hardware or software to control operation of the first smart device 250C, the second smart device 250D, or both smart devices 250C and 250D. In one example, the first smart device 250C or the second smart device 250D can comprise a smartphone, a smartwatch, or any other smart device capable of providing tactile stimulus pulses.

In one example, the smart device can be any suitable wireless device, such as a user equipment (UE), a mobile station (MS), a mobile wireless device, a mobile communication device, a tablet, a handset, or other type of wireless device. The wireless device can include one or more antennas configured to communicate with a node, macro node, low power node (LPN), or transmission station, such as a base station (BS), an evolved Node B (eNB), a baseband processing unit (BBU), a remote radio head (RRH), a remote radio equipment (RRE), a relay station (RS), a radio equipment (RE), or other type of wireless wide area network (WWAN) access point. The wireless device can be configured to communicate using at least one wireless communication standard such as, but not limited to, 3GPP 5G, 3GPP LTE, WiMAX, High Speed Packet Access (HSPA), Bluetooth, and WiFi. The wireless device can communicate using separate antennas for each wireless communication standard or shared antennas for multiple wireless communication standards. The wireless device can communicate in a wireless local area network (WLAN), a wireless personal area network (WPAN), and/or a WWAN. The wireless device can also comprise a wireless modem. The wireless modem can comprise, for example, a wireless radio transceiver and baseband circuitry (e.g., a baseband processor). The wireless modem can, in one example, modulate signals that the wireless device transmits via the one or more antennas and demodulate signals that the wireless device receives via the one or more antennas.

The first smart phone 250C or second smart phone 250D can further comprise a microphone and one or more speakers that can be used for audio input and output from the wireless device. The display screen can be a liquid crystal display (LCD) screen, or other type of display screen such as an organic light emitting diode (OLED) display. The display screen can be configured as a touch screen. The touch screen can use capacitive, resistive, or another type of touch screen technology. An application processor and a graphics processor can be coupled to internal memory to provide processing and display capabilities. A non-volatile memory port can also be used to provide data input/output options to a user. The non-volatile memory port can also be used to expand the memory capabilities of the wireless device. A keyboard can be integrated with the wireless device or wirelessly connected to the wireless device to provide additional user input. A virtual keyboard can also be provided using the touch screen.

Figure 2D:
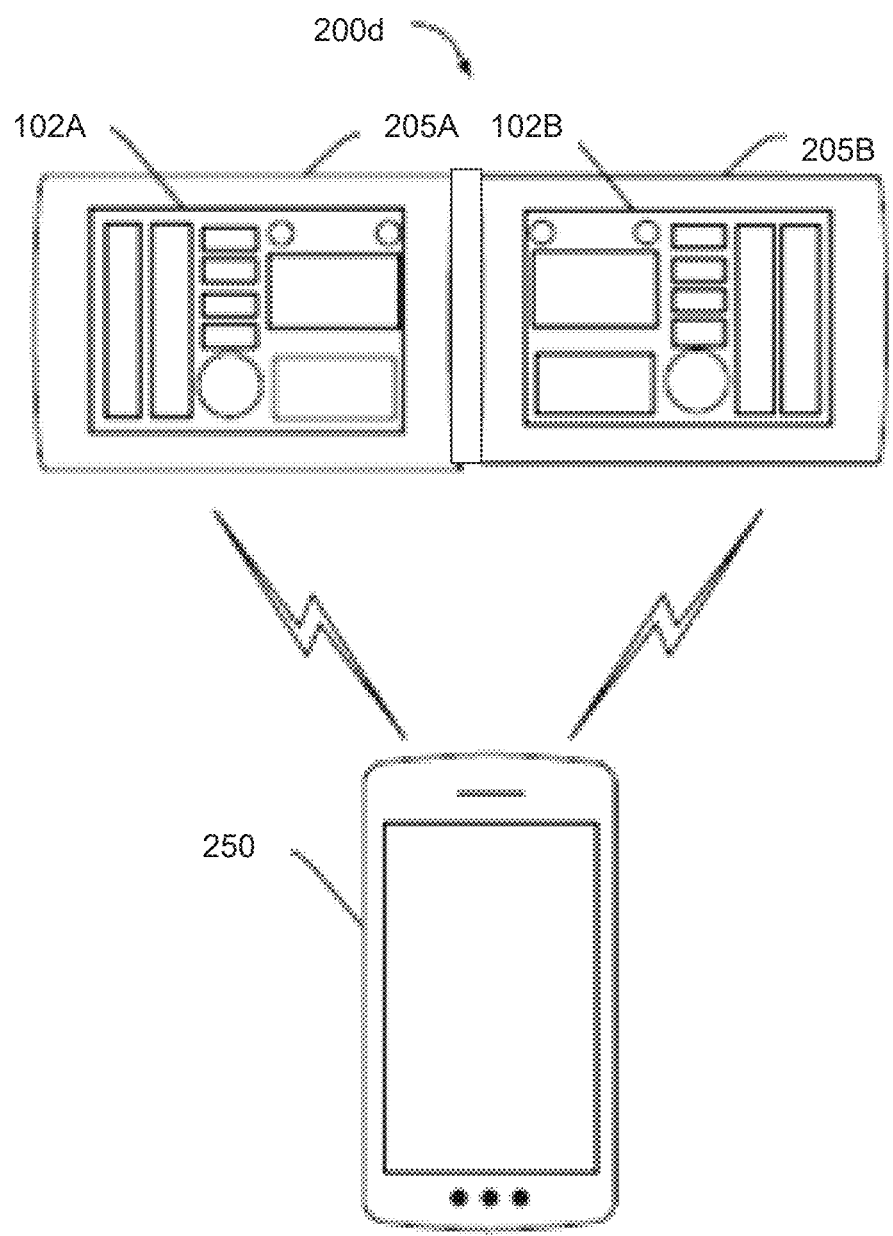
FIG. 2d depicts a bilateral stimulation system with modular devices, in accordance with some examples of the present disclosure.

In yet another non-limiting example, a BLS system 200d, as illustrated in FIG. 2D can comprise a first BLS device 102A and a second BLS device 102B that can each be configured to communicate with a remote device 250. In this example, the first and second BLS devices 102A and 102B can be modular with each BLS device including one or more vibration stimulators. In one example, the first BLS device 102A can be combined with the second BLS device 102B to form a single module 102A, 102B. The combined device 102A, 102B can deliver a BLS tactile stimulus from each individual BLS device 102A and 102B. In some cases, the individual devices 102A and 102B can each be coupled to a flexible article 205A and 205B, respectively.

When the single module 102A, 102B is formed, each tactile stimulus can comprise resonant frequencies that can provide a therapeutic effect to the end user. The single module 102A, 102B can be configured to provide a synergistic effect that can be perceived by the end user as a bilateral stimulus or as a unilateral stimulus. The first BLS device 102A can be physically coupled to the second BLS device 102B using various coupling devices including a pivot, a hinge, a swivel, the like, or combinations thereof.

In one example, the single module 102A, 102B can be positioned in the proximity of the centerline of the body, with one-part 102A of the single module 102A, 102B on one half (e.g., the left side) of the body and the other portion 102B of the single module 102A, 102B on the other half (e.g., the right side) of the body. Each portion 102A or 102B of the single module 102A, 102B can be configured to provide a vibrational frequency to generate resonance that provides a therapeutic effect to the end user.

The single module 102A, 102B can achieve a synergistic effect when the vibrations are configured at resonant frequencies. The vibration frequencies or patterns for each side of the body of the user can produce a combination of transient stimulations perceived as unilateral or bilateral. Thus, the single module 102A, 102B can produce bilateral stimulation even when located near the centerline of the body. Delivering bilateral stimulation at or near the centerline of the body of the user can target specific areas of the user's body including the centerline of the spine, the centerline of the oral cavity, the centerline of the face, the centerline of the head, the centerline of the cranial area, the like, or combinations thereof. In some examples, the resonant frequencies can achieve a synergistic effect that can increase or decrease according to a predetermined pattern or a randomly generated pattern. Resonant frequencies can be selected to achieve a particular therapeutic effect.

The single module 102A, 102B can comprise a plurality of tactile stimuli that can synchronize in phase or out of phase to generate a magnified level of resonance that is randomized, alternated, accelerated, decelerated, or reversed to provide a therapeutic benefit. Stacking the vibrations generated by the plurality of tactile stimuli can be effectuated by using one or more processors. The one or more processors can be configured to magnify the provided tactile energy or the perceived tactile energy generated by the individual tactile stimuli. Because low frequency wave forms can use a high amount of power in comparison to higher frequency wave forms, combining frequencies can generate the lower frequency wave forms using a lower amount of energy.

Figure 3:
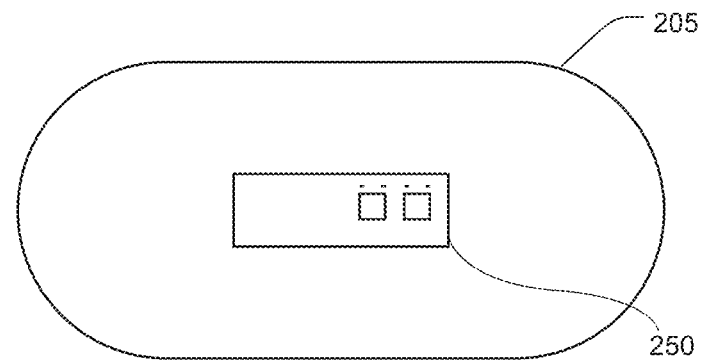
FIG. 3 depicts a bilateral stimulation system associated with a travel pillow, in accordance with some examples of the present disclosure.
Figure 3:
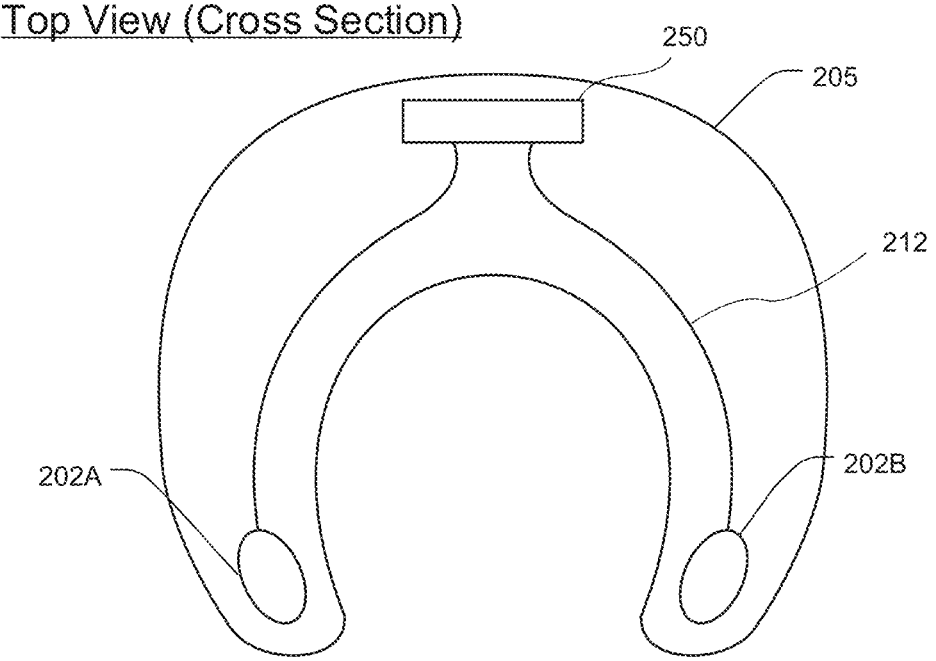

For example, as illustrated in FIG. 3, BLS devices 202A, 202B can be connected via wire connection 212 to a common control unit 250. In this particular example, the BLS devices 202A, 202B and common control unit 250 are each incorporated into a common flexible article 205 (e.g. travel or neck pillow). In this example, it may be desirable to construct the BLS devices 202A, 202B simply. For example, in some cases, the BLS devices 202A, 202B can be entirely powered and controlled via the common control unit 250. Where this is the case, the control unit 250 can include a power module, control module, communications module, data module, and other hardware or software to control operation of the BLS devices 202A, 202B. Further, in some examples, the control unit 250 can include one or more switches, a display, one or more indicators (e.g. LED indicators), and/or the like to facilitate operation of the system from the control unit 250. In some examples, the BLS devices 202A, 202B can be configured to include tactile stimulators without auditory stimulation. In other examples, the BLS devices 202A, 202B can be configured to include auditory stimulation and/or instructions without tactile stimulators. In still other examples, the BLS devices 202A, 202B can be configured to include tactile stimulators and auditory stimulation and/or instructions.

Figure 4:
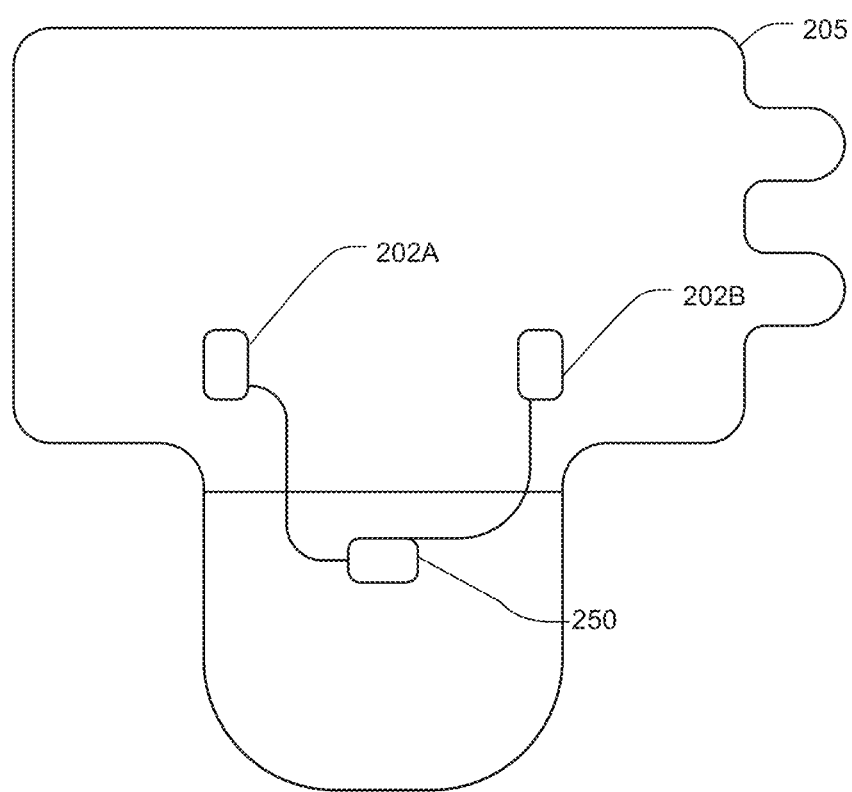
FIG. 4 depicts a bilateral stimulation system associated with an infant blanket, in accordance with some examples of the present disclosure.

Similar embodiments are illustrated in FIGS. 4-8. In further detail, FIG. 4 illustrates a BLS system including a pair of BLS devices 202A, 202B connected to a control unit 250 via a wired connection. In this example, the BLS devices 202A, 202B and common control unit 250 are coupled to a flexible article 205 that may be wearable and donned by a user, (e.g. a body wrap or smock such as a Snuggie™). It is noted that where a single flexible article is intended to be used for BLS treatment, it can be desirable to space individual tactile stimulators or corresponding BLS devices sufficiently far apart to allow the brain to be able to differentiate between left and right stimuli. For example, where tactile stimulators are employed, it can be desirable to space the left tactile stimulator(s) or corresponding BLS device(s) (e.g. 202A) at least 3", at least 4", at least 5", or at least 6" apart from right tactile stimulator(s) or corresponding BLS device(s) (e.g. 202B).

Figure 5:
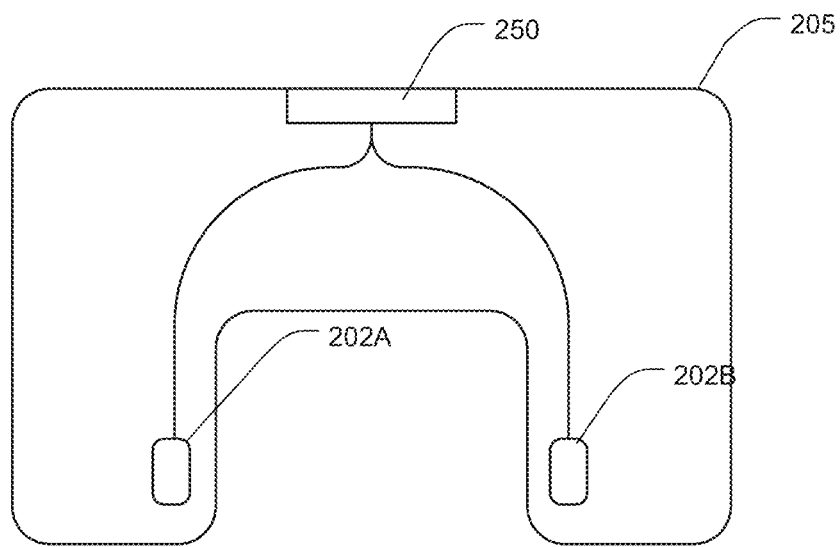
FIG. 5 depicts a bilateral stimulation system associated with a shoulder wrap, in accordance with some examples of the present disclosure.

FIG. 5 illustrates a BLS system including a pair of BLS devices 202A, 202B connected to a control unit 250 via a wired connection. In this example, the BLS devices 202A, 202B and common control unit 250 are coupled to a flexible article 205 (e.g. a weighted shoulder wrap). Some non-limiting example dimensions are also illustrated in FIG. 5. In this particular example, the weighted shoulder wrap is indicated as being 20"×14", but other suitable dimensions can also be used. A weighted shoulder wrap having these particular dimensions can typically have a weight of from about 4 pounds to about 6 pounds, or about 5 pounds. The ratio of the recited dimensions to the weight can also be used to scale the flexible article to other sizes, as desired.

Figure 6:
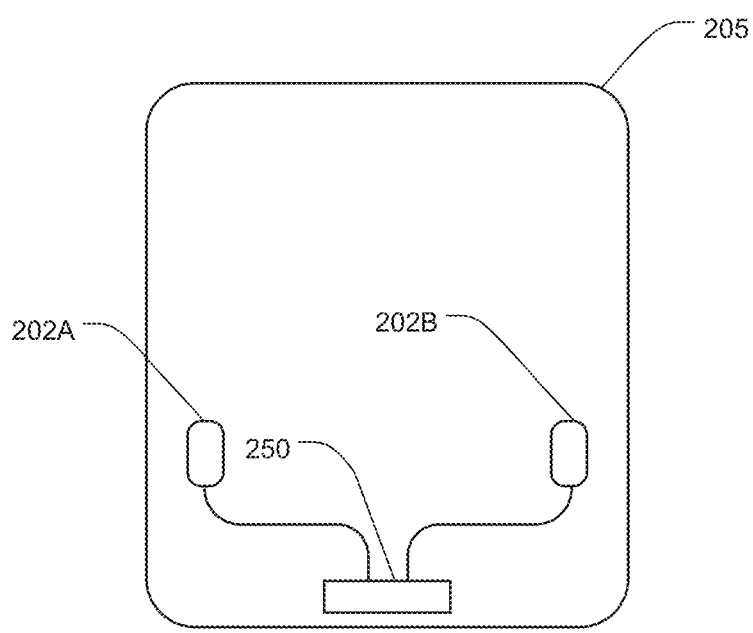
FIG. 6 depicts a bilateral stimulation system associated with a body pillow, in accordance with some examples of the present disclosure.

FIG. 6 illustrates a BLS system including a pair of BLS devices 202A, 202B connected to a control unit 250 via a wired connection. In this example, the BLS devices 202A, 202B and common control unit 250 are coupled to a flexible article 205 which is an unwearable article (e.g. a weighted chest pillow). Some non-limiting example dimensions are also illustrated in FIG. 6. In this particular example, the weighted chest pillow is indicated as being 12"×12", but other suitable dimensions can also be used. A weighted chest pillow having these particular dimensions can typically have a weight of from about 4 pounds to about 6 pounds, or about 5 pounds. In other examples, the weighted chest pillow can be about 14"×14" and have a weight of from about 6 pounds to about 8 pounds, or about 7 pounds. In still other examples, the weighted chest pillow can be about 16"×16" and have a weight of from about 8 pounds to about 10 pounds, or about 9 pounds. The ratio of the recited dimensions to the weight can also be used to scale the flexible article to other sizes, as desired. Also, while the listed dimensions indicate that the weighted chest pillow has a substantially square shape, this is also not required. The weighted chest pillow can have any suitable geometry.

Figure 7:
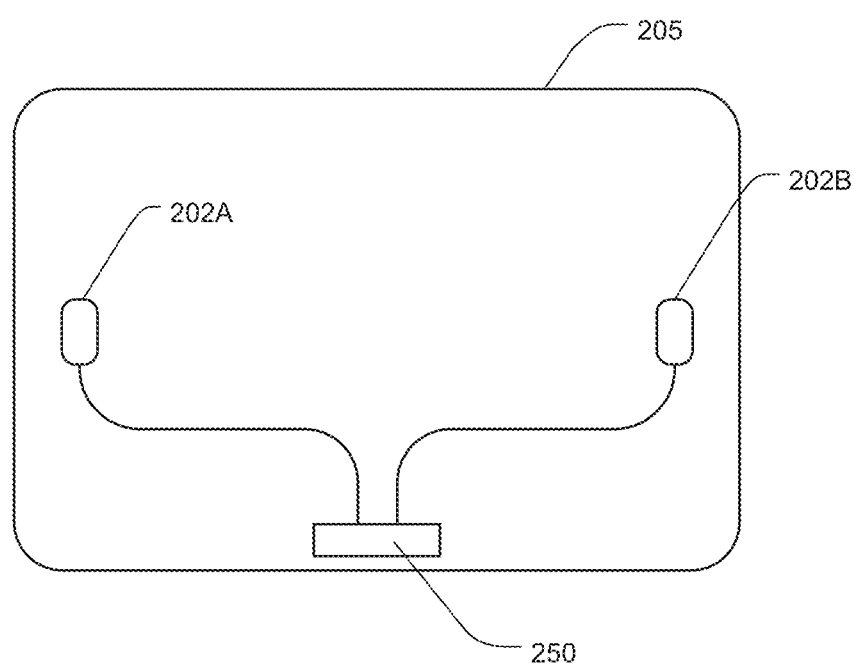
FIG. 7 depicts a bilateral stimulation system associated with a lap pad, in accordance with some examples of the present disclosure.

FIG. 7 illustrates a BLS system including a pair of BLS devices 202A, 202B connected to a control unit 250 via a wired connection. In this example, the BLS devices 202A, 202B and common control unit 250 are coupled to a flexible article 205 (e.g. a weighted lap pad). Some non-limiting example dimensions are also illustrated in FIG. 7. In this particular example, the weighted lap pad is indicated as being 18"×9", but other suitable dimensions can also be used. A weighted lap pad having these particular dimensions can typically have a weight of from about 3 pounds to about 4 pounds, or about 3.5 pounds. In other examples, the weighted lap pad can be about 24"×9" and have a weight of from about 4 pounds to about 6 pounds, or about 5 pounds. In still other examples, the weighted lap pad can be about 24"×12" and have a weight of from about 6 pounds to about 8 pounds, or about 7 pounds. The ratio of the recited dimensions to the weight can also be used to scale the flexible article to other sizes, as desired. Also, while the listed dimensions indicate that the weighted lap pad has a substantially rectangular shape, this is also not required. The weighted lap pad can have any suitable geometry.

Figure 8:
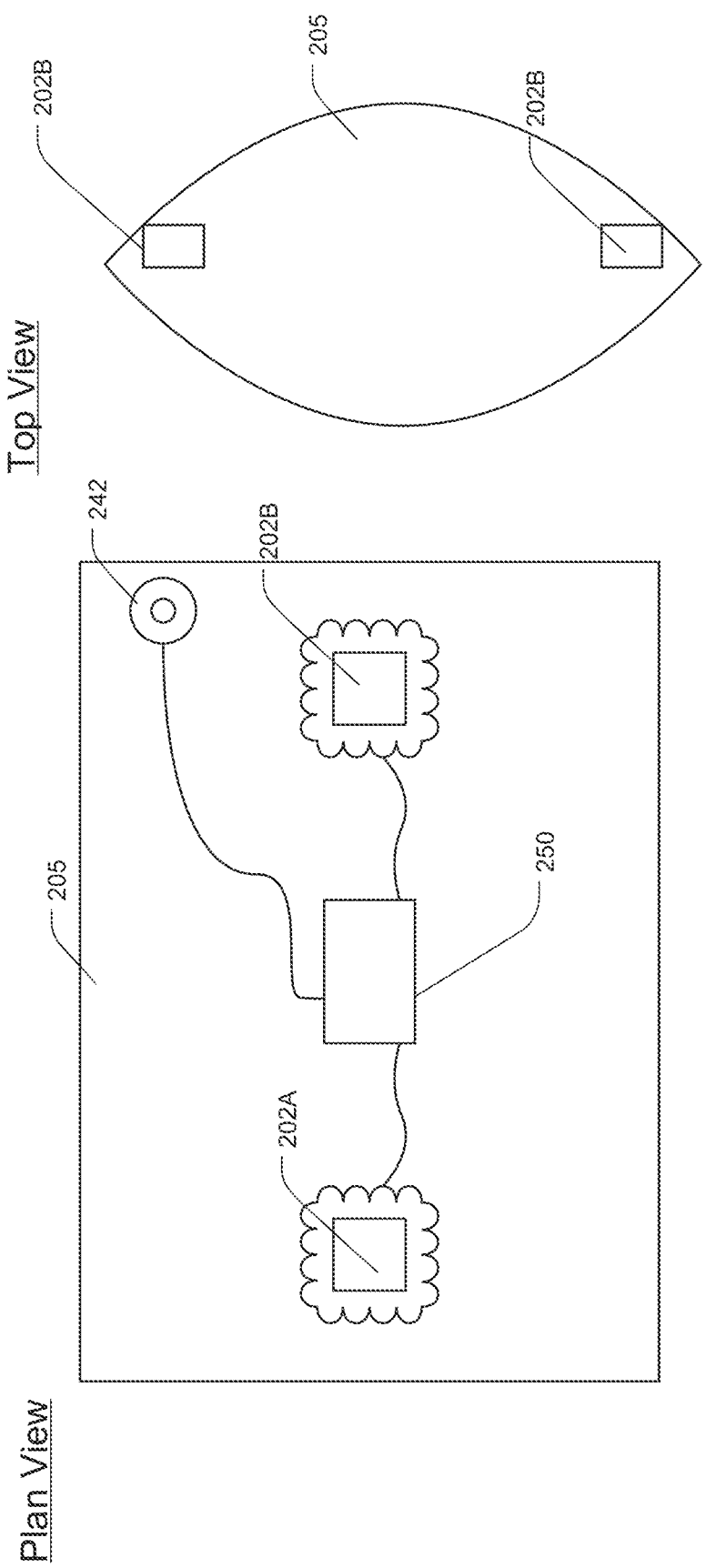
FIG. 8 depicts a bilateral stimulation system associated with a head pillow, in accordance with some examples of the present disclosure.

FIG. 8 illustrates a BLS system including a pair of BLS devices 202A, 202B connected to a control unit 250 via a wired connection. In this example, the BLS devices 202A, 202B and common control unit 250 are coupled to a flexible article 205 (e.g. a head pillow). In some examples, the flexible article of the BLS system can include a pillow case and a generic pillow can be inserted into the pillow case. Where this is the case, the pillow case can optionally include a zipper or other suitable features to retain the pillow inside and/or properly positioned within the pillow case. In other examples, the flexible article of the BLS system can include the pillow itself, which can fit within a generic pillow case. The same can be the case with other articles as well, such as weighted pillows mattresses, etc., where the flexible article can be either a covering that goes over a generic article, or the flexible article can be the pillow, mattress, etc. itself. Where one or more BLS devices are incorporated into a thick article, it can be desirable to position the individual BLS devices as close to the surface as reasonably possible. For example, where the BLS devices are positioned too deeply within a thick flexible article, tactile stimulation or auditory stimulation can become too weak to be effective. Thus, in some examples, the BLS devices can be positioned less than 1", less than 0.5", or less than 0.25" from the exterior surface of the article.

As can be seen from FIGS. 2-8, BLS systems can include a plurality of BLS devices associated with a common flexible article. As can also be seen from FIGS. 2-8, a plurality of BLS devices can be associated with individual respective flexible articles. In some further examples, BLS systems can include a plurality of flexible articles each including a plurality of BLS devices. Also, as can be seen from FIGS. 2-8, individual BLS devices can be connected via wireless connection or wired connection.

As described above, BLS systems can include a variety of BLS device configurations. For example, in some cases, BLS systems can include a single pair of BLS devices. In other examples, BLS systems can include multiple pairs of BLS devices (or a plurality of left BLS devices and a plurality of right BLS devices, not necessarily in pairs or equal in number). In some further examples, two or more BLS devices can be configured to include one or more tactile stimulators to perform BLS treatments. In other examples, two or more BLS devices can be configured to include one or more tactile stimulators configured to deliver a sustained tactile stimulus, rather than a pulsed tactile stimulus. In still other examples, one or more BLS devices can be configured to include a biofeedback sensor to collect heart rate data, breathing data, or the like to help regulate the end user's heart rate, breathing, and/or the like. In some examples, the BLS system can include a biofeedback sensor that is separate from a BLS device but is nonetheless connected or paired (e.g. wired or wireless) with the BLS system to provide biofeedback data to control one or more of the BLS devices of the BLS system. In yet other examples, one or more BLS devices can be configured to include one or more speakers configured to play an auditory stimulus in the frequency range of 20-50 Hz simulating a cat purr or the like. In other examples, one or more BLS devices can be configured to include one or more speakers configured to provide biofeedback (e.g. playing a particular tone or verbal instruction indicating the user needs to breath in a particular pattern, a particular tone or verbal instruction prompting the user to engage in isometric exercises or other activities to help regulate heart rate, etc.).

As one specific example, to help illustrate the versatility of the present BLS systems, a wristband or other suitable flexible article can include one or more attachment sites (e.g. 1-3 attachments sites, for example). Attachment sites can include pockets, pouches, snaps, zippers, clips, clamps, magnets, hook and loop fasteners, the like, or a combination thereof to facilitate attachment of one or more BLS devices thereto. The flexible article can be made to stretch in order to fit a number of different areas of the body, such as the arms, wrist, ankles, legs, waist, etc. In some examples, the various BLS devices can each be removably attachable to the flexible article. In other examples, one or more BLS devices can be permanently attached to the flexible article and one or more BLS devices can be removably attachable to the flexible article. In other examples, the various BLS devices can each be permanently attached to the flexible article. Non-limiting examples of BLS devices can include BLS devices specifically configured to perform BLS treatments via synchronized tactile stimulation, BLS devices configured to provide auditory frequencies simulating a cat purr (or other suitable auditory stimulus), BLS devices configured to provide biofeedback, etc. Thus, the BLS systems can be configured to provide simultaneous tactile BLS treatment with auditory stimulus (e.g. cat purr, or other suitable auditory stimulus), simultaneous tactile BLS treatment with biofeedback, simultaneous auditory stimulus (e.g. cat purr, or other suitable auditory stimulus) with biofeedback, or simultaneous tactile BLS treatment with auditory stimulus and biofeedback, for example.

In another specific example, a BLS system can comprise one or more of: a biofeedback sensor, software, external devices, memory, processor(s), artificial intelligence, the like, or combinations thereof. Each of these components of the BLS system can be configured to wirelessly or via a wired connection communicate with BLS devices to: (a) receive input from a user, (b) adjust tactile programs, (c) store data, and (d) analyze data based on input received from the user in real-time. In one example, a tactile program can command one or more tactile events (e.g., vibration events), such as, tactile pulses comprising: synchronous and asynchronous patterns, sequences, ramps, transitions, accelerations, decelerations, sustained patterns, un-sustained patterns, overlapping patterns, discrete patterns, conjoined patterns, non-conjoined patterns, the like, or combinations thereof. In one example, AI can include, but is not limited to, instructions embodied on a non-transitory computer readable medium that can be executed by one or more processors at a device when received via wired or wireless communication.

The BLS systems described herein can be used to perform bilateral stimulation and other therapeutic methods to treat or otherwise ameliorate an adverse health condition. For example, the BLS systems can be used to apply sustained and/or alternating vibrational bilateral stimulation (BLS) pulses to a subject at a therapeutic vibrational frequency for a treatment period. Typically, the alternating vibrational BLS pulses are delivered to the subject at locations that are sufficiently separated to allow the brain to differentiate between left and right stimuli. In some examples, this can be a separation distance of at least 3", at least 4", at least 5", at least 6", or more. Where a sufficient separation is achieved for the brain to distinguish between left and right stimuli, this can be referred to herein as right and left sides of the body, or opposite sides of the body, whether or not the positioning of the stimuli is actually on different sides of the body or opposite sides of the body. For example, both stimuli may be delivered entirely on the right side of the body or entirely on the left side of the body, but at a sufficient separation distance for the brain to differentiate between left and right stimuli. This can be referred to herein as left and right sides of the body and/or opposite sides of the body. However, in some specific examples, the alternating tactile BLS pulses can be delivered to an actual rights side of the body and an actual left side of the body (not just perceived right and left stimuli).

In further detail, tactile stimulus pulses can typically be performed at a vibrational frequency of from about 5 Hz to about 400 Hz. In some further examples, the tactile stimulus pulses can be performed at a vibrational frequency of from about 20 Hz to about 100 Hz. In additional examples, the tactile stimulus pulses can be performed at a vibrational frequency of from about 20 to about 75 Hz. In still additional examples, the tactile stimulus pulses can be performed at a vibrational frequency of from about 75 Hz to about 95 Hz.

For example, in some cases, it can be desirable to use vibrational frequencies of from about 20 Hz to about 75 Hz to treat physical conditions or symptoms, whereas it can be desirable to use vibrational frequencies of from about 75 Hz to about 95 Hz to treat emotional conditions or symptoms. Thus, in some cases, a first tactile stimulus pulse can be performed at a first vibrational frequency (e.g. from about 20 Hz to about 75 Hz) and a second tactile stimulus pulse can be performed at a second vibrational frequency (e.g. from about 75 Hz to about 95 Hz). As such, in some examples, the methods can be used to treat both physical and emotional conditions and/or symptoms.

In other examples, tactile stimulus pulses can be performed at a vibrational frequency that can be selected to treat or otherwise ameliorate an adverse health condition. In one example, the vibrational frequency can be adjusted based on a biofeedback sensor, such as a heart rate sensor, a brain wave sensor, a perspiration sensor, a muscle tension sensor, a nerve conduction sensor, an optical sensor, the like, or a combination thereof.

Individual tactile pulses can be performed for a variety of time periods, depending on the condition to be treated. In some examples, individual tactile pulses can have a duration of from about 0.5 seconds to about 2.0 seconds. In some other examples, individual tactile pulses can have a duration of from about 0.6 to about 1.0 seconds, about 0.7 seconds to about 0.9 seconds, or about 0.8 seconds. More specifically, individual tactile pulses can alternate from side-to-side in a rhythmic pattern. For example, each side will employ a tactile pulse, as described above, followed by a tactile pause. Individual tactile pauses on a given side of the body can typically have a duration of from about 0.1 seconds to about 2.0 seconds. In some other examples, individual tactile pauses can be from about 1.0 seconds to about 1.4 seconds, about 1.1 seconds to about 1.3 seconds, or about 1.2 seconds. In some examples, a plurality of tactile pulses can be delivered on a common side of the body prior to delivering a tactile pulse on the other side of the body (e.g. 2 or 3 tactile pulses).

It is noted that, because the method can include alternating BLS tactile stimulus pulses, a tactile stimulus pulse on one side of the body can overlap with a tactile pause on the other side of the body. In some examples, the tactile pause can be longer than the tactile stimulus. Where this is the case, there can be a brief tactile gap between alternating tactile stimuli where no tactile stimulus occurs on either side of the body. In other examples, the tactile stimulus pulse duration can be the same as the tactile pause duration. Where this is the case, there is no tactile gap because alternating tactile stimuli commence at the same time as alternating tactile pauses on the opposite side of the body. In still other examples, as described above, a plurality of stimuli can be delivered on a common side of the body before delivering a plurality of stimuli on the opposite side of the body (this sequence being repeatable in a side-to-side pattern). In yet another example, the tactile pause duration can be applied to any and all BLS devices to stop tactile stimuli until the tactile pause duration has ended.

In some examples, the tactile stimulus can be delivered on both sides in a sustained pulse. The sustained pulse can also be performed within the frequency ranges disclosed above. In some specific examples, the sustained pulse can be applied at a vibrational frequency of from about 20 Hz to about 75 Hz. In some examples, the sustained pulse can be maintained for the entire treatment period. In other examples, the sustained pulse can include an interim pause at pre-determined intervals, such as those already described herein.

In some examples, it can be desirable to have an interim pause after a number of pulse/pause cycles. The interim pause can be valuable to help calm the brain and refocus thought during the treatment period. In some examples, an interim pause can be performed at a rate of from about every 15 to about 45 cycles of alternating BLS stimuli (one cycle including one left tactile stimulus and one right tactile stimulus), or from about every 20 to about 40 cycles of alternating BLS stimuli. In some additional examples, it can be desirable to perform an interim pause at certain points during the treatment period, whether or not pulse/pause cycles are employed. For example, the interim pause can occur at a rate of from every 20 seconds to 120 seconds, every 30 seconds to every 90 seconds, every 45 seconds to every 75 seconds, or about every 60 seconds. In some other examples, the interim pause can be performed at least once, at least twice, at least three times, four times, five times, or more during the treatment period. The interim pause itself can typically have a duration of from about 5 seconds to about 5 minutes. In some specific examples, the interim pause can have a duration of from about 5 to about 10 seconds, about 6 to about 8 seconds, or about 7 seconds. In some additional examples, the interim pause can have a duration of from about 10 seconds to about 60 seconds, from about 30 seconds to about 90 seconds, from about 60 seconds to about 120 seconds, from about 90 seconds to about 180 seconds, from about 120 seconds to about 240 seconds, or from about 180 seconds to about 300 seconds.

In other examples, the duration of the tactile stimulus pulse and the duration of the interim pause can be adjusted based on a set of pre-determined treatment modalities. Specific memory rewiring methods, such as eye movement desensitization and reprocessing, can be used in conjunction with the set of pre-determined treatment modalities. For example, a pre-determined number of alternating tactile bilateral stimulations may occur in repetitive patterns that can be interrupted by an intermittent pause of a selected duration.

The treatment period can generally be a period of from about 5 minutes to about 120 minutes. In some specific examples, the treatment period can be about 5 minutes, about 10 minutes, about 15 minutes, about 20 minutes, about 25 minutes, about 30 minutes. In additional examples, the treatment period can be about 45 minutes, about 60 minutes, about 75 minutes, about 90 minutes, about 105 minutes, or about 120 minutes. In some further examples, the treatment period can be from about 5 minutes to about 10 minutes, from about 10 minutes to about 15 minutes, from about 15 minutes to about 20 minutes, from about 20 minutes to about 25 minutes, or from about 25 minutes to about 30 minutes. In still additional examples, the treatment period can be from about 30 minutes to about 45 minutes, about 45 minutes to about 60 minutes, about 60 minutes to about 75 minutes, about 75 minutes to about 90 minutes, about 90 minutes to about 105 minutes, or about 105 minutes to about 120 minutes.

In some further examples, the method can include a diminishing intensity fade over a desired period of time. As one non-limiting example, the method can employ a linear diminishing intensity fade over the last 10% to 100%, 5% to 50%, or 3% to 30% of the treatment period. Of course, non-linear intensity fades can also be used, as desirable. Further, the specific duration of the intensity fade can also be adjusted, as desirable. In some specific examples the last 1 minute to 30 minutes (e.g. the last 30 minutes, 20 minutes, 10 minutes, 5 minutes, 3 minutes, 2 minutes, etc.) of the treatment period can include a linear (or non-linear) intensity fade such that the intensity diminishes (ramps down) linearly from 100% of an operating intensity level and is reduced progressively down to 10% of the operating intensity level before automatically turning off the BLS device. In some cases, 20% of the operating intensity level can be the upper signal threshold level that most end users can easily discern.

Individual alternating tactile stimulus pulses can be performed at a sufficient tactile intensity to provide an effective treatment. For example, if the tactile intensity is too low, the tactile stimulus may be too weak to be therapeutically effective. However, if the tactile intensity is too strong, the stimulus may be overbearing, distracting, loud, etc., which can also decrease the therapeutic benefit of the stimulus.

Regardless of the tactile intensity, in some examples, it can be desirable for the alternating tactile stimulus pulses to be performed discretely. For example, in some cases, alternating tactile stimulus pulses can be performed at a decibel level at or below 35 decibels at a distance of 0.5 m or less from the site of the tactile stimulus. In some additional examples, alternating tactile stimulus pulses can be performed at a decibel level at or below 30 decibels at a distance of 0.5 m or less from the tactile stimulus. In other examples, alternating tactile stimulus pulses can be performed at a decibel level at or below 25 decibels at a distance of 0.5 m or less from the tactile stimulus. In still other examples, alternating tactile stimulus pulses can be performed at a decibel level of from about 25 decibels to about 35 decibels at a distance of 0.5 m or less from the tactile stimulus.

In other examples, the tactile stimulator can be configured to have a decibel level at or below a selected intensity at a selected distance from the tactile stimulator. In one example, the selected intensity, the selected distance, or both can be adjusted based on a proximity sensor. For example, when the proximity sensor detects the presence of a non-user in the selected distance, the intensity of the tactile stimulus pulses can be reduced to provide discreteness. In another example, the intensity of the tactile stimulus pulses can be increased when the proximity sensor detects that a non-user is located outside the selected distance.

The tactile stimulator can be configured to have various settings including one or more of: vibrational frequency, vibrational intensity, vibrational speed, vibrational acceleration, vibrational duration, vibrational pause, vibrational patterns sets of vibrational patterns, the like, or combinations thereof. In one embodiment, the amount of vibration can be an amount sufficient to be recognized by a user. In another embodiment, the amount, degree, or characteristics of the vibration can be a minimum amount required for detection by a user. In another embodiment, the amount, degree, or characteristics of the vibration can be a minimum amount required for detection by a user at a specific anatomical location, such as an ankle, a wrist, a lower back, a forehead, a neck or side of the neck, a chest, a foot, etc. In yet another embodiment, the amount, degree, or characteristics of the vibration can be more than a minimum amount required for detection by a user. In one embodiment, the amount can be from about 1 time to 10 times greater than a minimum amount required for detection by a user either when or when not in a specific anatomical location.

In some examples, a plurality of tactile stimulus methods can be applied to a subject concurrently. For example, in some cases, alternating tactile stimuli can be applied to the subject concurrently with a sustained tactile stimulus. In further detail, sustained tactile stimuli can be applied concurrently to both sides of the body, but at a different vibrational frequency than the vibrational frequency employed with the alternating tactile stimulus pulses being simultaneously applied to the subject. In other examples, two different alternating tactile stimulus methods can be applied simultaneously to the subject. Where this is the case, the separate alternating tactile stimulus methods can have different vibrational frequencies, different pulse durations, different pause durations, different interim pause frequency, different interim pause duration, the like, or a combination thereof.

In some examples, the method can include auditory stimulus pulses in addition to or separate from the alternating or sustained tactile stimuli described elsewhere herein. The auditory stimulus pulses can typically be performed at a frequency of from about 5 to about 400 hertz (Hz). In some further examples, the auditory stimulus pulses can be performed at a vibrational frequency of from about 20 to about 100 Hz. In additional examples, the tactile stimulus pulses can be performed at a vibrational frequency of from about 20 to about 75 Hz. In still additional examples, the tactile stimulus pulses can be performed at a vibrational frequency of from about 75 to about 95 Hz. In some specific examples, the auditory stimulus pulses can be at a frequency of from about 20 to about 50 Hz to simulate a cat purr.

In some specific examples, individual auditory stimulus pulses can alternate from side to side. Where this is the case, individual auditory stimulus pulses can have a duration of from about 0.5 to about 2.0 seconds. In some other examples, individual auditory stimulus pulses can have a duration of from about 0.6 to about 1.0 seconds, about 0.7 to about 0.9 seconds, or about 0.8 seconds. As with the tactile stimulus pulses, individual auditory pauses can be performed between individual auditory stimulus pulses on a given side of the body. Individual auditory pauses on a given side of the body can typically have a duration of from about 0.1 seconds to about 2.0 seconds. In some other examples, individual tactile pauses can be from about 1.0 seconds to about 1.4 seconds, about 1.1 seconds to about 1.3 seconds, or about 1.2 seconds.

As described above with respect to the tactile stimulus pulses/pauses, an individual auditory stimulus pulse on one side of the body can overlap with an individual auditory pause on the other side of the body. In some examples, the auditory pause can be longer than the auditory stimulus. Where this is the case, there can be a brief auditory gap between alternating auditory stimuli where no auditory stimulus occurs on either side of the body. In other examples, the auditory stimulus pulse duration can be the same as the auditory pause duration. Where this is the case, there is no auditory gap because alternating auditory stimuli commence at the same time as alternating auditory pauses on the opposite side of the body. In still other examples, a plurality of auditory stimuli can be delivered on a common side of the body before delivering a plurality of auditory stimuli on the opposite side of the body (this sequence being repeatable in a side-to-side pattern).

In some examples, it can be desirable to have an interim pause after a number of auditory pulse/pause cycles. The interim pause can be valuable to help calm the brain and refocus thought during the treatment period. In some examples, an interim pause can be performed at a rate of from about every 15 to about 45 cycles of alternating auditory stimuli (one cycle including one left auditory stimulus and one right auditory stimulus), or from about every 20 to about 40 cycles of alternating auditory stimuli. In some additional examples, it can be desirable to have an interim pause at various points during the treatment period, whether or not pulse/pause cycles are employed. For example, the interim pause can occur at a rate of from every 20 seconds to 120 seconds, every 30 seconds to every 90 seconds, every 45 seconds to every 75 seconds, or about every 60 seconds. In some other examples, the interim pause can be performed at least once, at least twice, at least three times, four times, five times, or more during the treatment period. The interim pause itself can typically have a duration of from about 5 seconds to about 5 minutes. In some specific examples, the interim pause can have a duration of from about 5 to about 10 seconds, about 6 to about 8 seconds, or about 7 seconds. In some additional examples, the interim pause can have a duration of from about 10 seconds to about 60 seconds, from about 30 seconds to about 90 seconds, from about 60 seconds to about 120 seconds, from about 90 seconds to about 180 seconds, from about 120 seconds to about 240 seconds, or from about 180 seconds to about 300 seconds.

In some examples, the alternating auditory stimulus pulse can be performed with a tactile stimulus pulse and can match a tactile stimulus pulse for frequency and/or pulse and pause duration. In some examples, the alternating auditory stimulus is performed concurrently with an alternating or non-alternating tactile stimulus, but does not match the tactile stimulus pulse for frequency and/or pulse and pause duration. In still other examples, the alternating auditory stimulus is performed without any tactile stimulus pulse. In yet additional examples, the alternating auditory stimulus pulse can be performed concurrently with two separate tactile stimuli methods where the auditory stimulus pulses match the vibrational frequency and pulse and pause duration of one tactile method, but not the other. For example, an alternating auditory stimulus regimen can match an alternating tactile stimulus regimen for frequency and pulse and pause duration and can be applied to the subject concurrently with a sustained tactile pulse at a different vibrational frequency.

In some additional examples, the auditory stimulus is not an alternating stimulus. For example, in some cases, the auditory stimulus can be applied concurrently to both sides of the body. In other examples, the auditory stimulus can be applied isolaterally in a sustained or pulsed manner. In some examples, the auditory stimulus can include a tone, music (e.g. classical music), sounds from nature, sounds recorded by the subject or a caregiver of the subject, automated instructions, etc.

In some examples, methods (or devices or systems) of the present invention can include a biofeedback component. In such a case, the methods of administering BLS can include monitoring a physiologic process or activity (e.g. heart rate or breathing rate) of the subject. In some specific examples, the monitoring can be performed via a biofeedback sensor, such as a heart rate sensor, a brain wave sensor, a perspiration sensor, the like, or a combination thereof. In some examples, a biofeedback stimulus can also be administered to the subject based on information collected by the biofeedback sensor. The biofeedback stimulus can include an indicator tone, auditory instructions, a mechanical stimulus, the like, or a combination thereof. The biofeedback stimulus can indicate to the user that the user needs to be breathing in a particular pattern, the user needs to engage in isometric exercises or other activities to help regulate heart rate, etc., for example. In some examples, the biofeedback stimulus can be administered concurrently with one or more tactile stimuli. In other examples, the biofeedback stimulus can be administered concurrently with one or more auditory stimuli. In other examples, the biofeedback stimulus can be administered concurrently with one or more visual stimuli. In still other examples, the biofeedback stimulus can be administered concurrently with one or more tactile stimuli, one or more auditory stimuli, and/or one or more visual stimuli. In yet other examples, the tactile stimulus regimen employed can be altered based on the data collected by a biofeedback sensor.

While biofeedback can be used in a number of ways, a few non-limiting examples of biofeedback methods are provided below. For example, in treating panic/anxiety, the biofeedback method can employ audio indicators that lead people through the following sequence of behaviors: regulated breathing (three seconds in, three seconds out for 2-3 minutes), isometric exercises (squeeze and hold for 6 seconds, three sets, total of 1.5-2 minutes), and deep breathing (five seconds in, five seconds out). Total time for this sequence can be about 5-6 minutes. Deep breathing can be continued for any desired amount of time, counting of breaths can continue to enhance meditative effect. Bilateral stimulations can be performed at a rate of 35-40 sets within about a 1-minute time frame. An optional interim pause (e.g. about 7 seconds) can be performed between one or more sets. For a sleep mode, audio indicators for deep breathing can be paced to enhance progression towards coherence with breathing in for 4-5 seconds and breathing out for 4-5 seconds for about 10-15 minutes. Bilateral stimulations can be performed at 18-20 sets within about a 1-minute time frame. An optional interim pause (e.g. about 7 seconds) can be performed between one or more sets.

In other examples, a BLS program can comprise tactile stimulation patterns (e.g., vibration programs) that can be synchronized in time with audio features, visual features, or combinations thereof. The BLS system can comprise processors and/or memory configured to produce a therapeutic effect. In one example, audio or visual features can be synchronized in time with intermittent pause patterns. In one example, the processors and/or memory can comprise artificial intelligence, software, augmented reality, smart devices, wireless communication, wired communication, or the like that can be configured to elicit, receive, or use a user's response to an interactive BLS program. In one example, the type of tactile stimulation can comprise any suitable tactile stimulation that can provide a desired or detectible/recognizable sensation including, but not limited to, one or more of: vibrational stimuli, linear stimuli, tapping stimuli, resonance-generated stimuli, touch-based stimuli, electro-stimulation, temperature-based stimuli (e.g., a hot stimuli having a temperature ranging from about 80° F. to about 140° F., or a cold stimuli having a temperature ranging from about 50° F. to about −10° F.), ultrasonic patterns, the like, or combinations thereof. In short, nearly any device or mechanism capable of providing a tactile sensation of which a user or subject can become aware or acknowledge can be used.

In another example, a BLS program can comprise an intermittent pause that can be synchronized in time with an audio or visual cue to produce a therapeutic effect. In one specific example, the BLS program can engage a subject in meditative exercises adequate to produce a therapeutic effect by rewiring memories and/or related neural association networks. This meditative exercise can have selected intermittent pause sequences that can be synchronized with selected audio or visual features to engage the subject in the meditative exercises.

In some additional examples, the method can include exposing the subject to a fragrance during administration of one or more tactile stimulus, one or more auditory stimulus, and/or a biofeedback stimulus, as described herein. The fragrance can include an essential oil, a fragrance obtained from a care-giver or other loved one, or other suitable fragrance.

A few specific, but non-limiting, examples of the present methods are described below. In one example, the method can be performed to ameliorate anxiety (e.g. high anxiety) or stress (e.g. high stress). In this example, 35-40 sets (each set including one right and one left stimulus) of alternating tactile stimulus pulses can be performed within about 1 minute followed by a 7 second interim pause. This process can be repeated for a treatment period of from about 5 minutes to about 20 minutes. In another example, the method can be used to ameliorate moderate stress. In this example, about 25 sets of alternating tactile stimulus pulses can be administered within about 1 minute followed by a 7 second interim pause. This process can be repeated for a treatment period of from about 5 minutes to about 20 minutes. In still other examples, the method can be used to help promote sleep/relaxation phase/process information (e.g. cognitive restructuring, use of positive scripts, managing negative self-scripts, and/or the like). In this example, 18-20 sets of alternating tactile stimulus pulses can be performed within about 1 minute followed by a 7 second interim pause. This process can be repeated for a treatment period of from about 5 minutes to about 20 minutes.

In some additional examples, the methods can perform one or more neurocognitive remodeling or brain rewiring "programs" (e.g., BLS programs) that can be adjusted and modified by a user in real-time to enhance an overall brain rewiring process, such as via biofeedback, software programming, the like, or a combination thereof. For example, software associated with a BLS device or system can include programs configured or programmed to enhance positive mental material and neutralize negative mental material. In some additional examples, the software programming can include pre-programmed guided exercises that can be done without the user providing real-time feedback. In some examples, the software programming can include AI software for the purpose of adjusting selected treatment programming based on biofeedback or other user input.

In further detail, the remodeling or rewiring programs can be configured or programmed to achieve specific therapeutic outcomes. For example, the following are provided by way of non-limiting examples of rewiring programs that can be incorporated in the BLS devices/systems described herein. In some examples, these programs can be interactive using audio or a combination of video and audio. In some examples, the programs can be pre-programmed and self-paced. In other examples, the programs can automatically update/adjust as needed based on AI programming associated with the BLS device/system.

Example Program 1: Enhancing Positive. BLS stimulations can be supplemented by a narrator, where the narrator or virtual caregiver guides the end user through a series of mental exercises. The exercises can teach meditations skills and direct the mind to focus on positive images in a method that allows positive and warm feelings to be implanted firmly in the mind for better recall and stronger emphasis in a way that builds confidence, peace, and appreciation. Users can also be prompted for feedback and the user response provides information that the AI programming can use to optimize material delivery to improve effectiveness and treatment outcomes Example Program 2: Reducing Negative. BLS stimulations can be supplemented by a narrator, where the narrator or virtual caregiver guides the end use through a series of mental exercises. The exercises teach meditations skills and direct the mind to focus on negative images and experiences in a method that allows the memories to be extracted or diminished from memory, and in some or many cases replaced with positive memories. This can be a powerful program, but it can require proper mental preparation (which the program can be programmed to provide). Thus, with proper discipline and focus, the undesirable memories can be deleted or overwritten with positive and warm feelings or memories. An immediate and longer-term benefit can be that the mind is purposefully conditioned to thereafter inherently put less emphasis on these specific negative aspects of life both consciously and subconsciously. Users can also be prompted for feedback during the session and the data from the user response can be used to provide information that the software programming can use to optimize delivery of treatment in order to improve effectiveness and reduce risk of negative side effects that can result if users become overwhelmed during the recall of sensitive topics or harsh experiences.

Example Program 3: Self-EMDR. BLS stimulations can be supplemented by a narrator, where the narrator or virtual caregiver guides the end user through a series of mental exercises. The exercises teach meditation skills and focus specifically on delivering EMDR processing principles. This can be a powerful program and it does necessarily require special guidance in order for the treatment to be both safe and effective. Nonetheless, self-EMDR can benefit from proper mental preparation (which the program is programmed to provide) and thus with proper discipline and focus, undesirable memories can be identified, rooted out, formally processes, and then reprocessed in a way to eliminate mental scaring or remove mental obstruction that can hinder rational mental processing of traumatic events. For example, PTSD events can become untangled and the full memories are extracted and reprocessed purposefully. The immediate and longer-term benefit can be that the mind is purposefully reconditioned and can thereafter inherently put less emphasis on these specific negative aspects of one's life both consciously and subconsciously. In this case, EMDR does not necessarily require eye movement, but it does utilize the bilateral stimulation via the tactile stimulators in contact with the left and ride sides of the user's body.

Thus, end users can be effectively guided through one or more of these, or other suitable, programs anywhere, on their schedule, and even on demand. Users can also be prompted for feedback during the session and the data from end users and/or bio feedback can be used to provide information that the software programming can use to dynamically optimize delivery of treatment regimes in order to improve effectiveness and reduce risk of negative side effects that may occur if users become overwhelmed during the mental recall of sensitive topics or harsh experiences. Furthermore, the speed and/or intensity of the bilateral pulses can be changed in real-time by the user via the device itself, without necessarily having to access the app. Additionally, the end user can also use push buttons to turn the device on and off, engage auto resume with push buttons, the like, or a combination thereof, without necessarily having to access the app. Thus, in some examples, the user can change process values (e.g. frequency and intensity) without removing hands from the device or without opening eyes (e.g. via a pair of physical buttons on the modules that update the global program values via wireless communication, for example). The physical buttons can have visual (e.g. colored LED) and/or physical cues in the design (e.g. stickers, labels, raised features, distinctive texture, printed letters, bosses, the like or a combination thereof). This can allow a user to intuitively interact or self-train with the device and make or use preferred adjustments while the user's eyes are closed.

Additionally, in some examples, program or treatment modules can start-up and operate as intended without engaging an app on the remote device, for example. In some examples, the user can start the modules quickly and seamlessly on demand. For example, default settings can be used, the user can change the settings to be custom or preferred by default. In some examples, the treatment modules can be initiated by pressing a button on a BLS device, using audio commands, the like, or a combination thereof, without having to rely on an app. In other examples, an app or other software of a remote device can be used to start a treatment module.

In some additional examples, the system can include a visual device (e.g. glasses, other visual augmented reality tools) to incorporate augmented reality into the BLS programs. For example, in some cases, the user will be able to view, through a visual device that is synced with the system programs and programming features to provide one or more visual components to the brain-rewiring programs described herein. Non-limiting examples of visual components that can be included are: (1) visualization of calm and relaxing places, people, and situations to enhance positive memories and mental material, which can be synced with the bilateral pulses and associated programs to enhance overall intensity of the experience; (2) visualization of negative mental material that the user is trying to desensitize (e.g. pictures of things that cause emotional triggers (i.e. triggering objects, places, and people); (3) visual prompts to aid the user in engaging in the brain rewiring process (e.g. a visual representation of the specific brain rewiring step the program is prompting the user to perform); (4) visual clues to aid the user in self-assessment measures (e.g. self-scaling questions), the answers to which can guide the direction of the brain rewiring program. In some examples, the users can seek or experience things via visual cues or stimuli and be able to respond to the program via audio (e.g. speech), such that the program can process the audio information received from the user and adjust the brain-rewiring program accordingly; (5) visual cues to aid the user in engagement of therapeutic self-help tools and resources; (6) visual cues synced with biofeedback data to aid the user in learning and enhancing specific calming and relaxation techniques; the like; or a combination thereof.

Additionally, the neurocognitive remodeling or brain rewiring programs can further employ biofeedback features, such as monitoring of heart rate, breathing, perspiration, and brain waves to determine the pacing and direction of brain rewiring programs. Biofeedback measures (e.g. elevated heart rate, higher palm sweat, fast breathing, or specific brain waves) for example, can be measured and the associated values can direct the user to engage in certain activities to decrease these symptoms to achieve a calmer state. For example, in some cases, the system will auto-select a specific brain rewiring program and prompt the user to engage in specific breathing or other calming techniques, or the like. This can be performed in conjunction with the bi-lateral pulses and synced with the specific brain rewiring programs associated with the system programming.

The use of biofeedback features can also be used in conjunction with external devices (e.g. toys, meditative technology and tools, etc.) to enhance the user's ability to learn specific calming and relaxation skills. These can be used in conjunction with the bilateral pulses as well. For example, while doing the bilateral pulses with the interim pause, users can engage in specific breathing techniques to achieve a specific calmed response. Once the user has obtained a certain calmed response as indicated by specific biofeedback data (e.g. specific heart rate, breathing rate, etc.), a secondary device may auto start a motor/fan in the object to make it run (e.g. make a toy car run), or allow the user to engage in a certain feature of a video game as seen in an optional visual device providing augmented reality features.

In further detail, in addition to enhancing calmed and relaxed mood states, bilateral stimulation can also help to rewire memory networks in that it can help to enhance positive mental imagery and decrease the intensity of negative memories. Without being bound by theory, it is believed that the brain does not store every detail of a memory, but rather stores the main features of a memory and fills in the rest with what is being experienced in the current moment while we are recalling that memory. Thus, some memories can change over time and some memories can become more positive while others can become more negative. This window of reconsolidation (i.e., the time frame of roughly one hour or so in which memories are more malleable after they have been recalled) can be used to change the nature of a memory in that if negative memories are able to be recalled during moments in which an individual feels calm and relaxed, the negativity of that memory can eventually become neutralized over time. Likewise, if an individual is able to recall a positive memory while feeling calm and relaxed and conjointly able to focus on the various positive features of that memory, the positive nature of that memory can be intensified.

Neutralizing negative memories can involve using the window of reconsolidation as negative memories are brought up and then switch the mind to think of a more positive memory, at first back and forth and then eventually simultaneously. This can help the brain to encode the positive features of the positive memory and associate them with the negative memory, thus eventually neutralizing the negative memory over time.

Enhancing positive memories can involve highlighting different aspects of the positive memory, including visual and audio stimuli, body sensations and emotions, and the intentions and actions the positive memory prompted you to take. Doing these mental tasks while thinking of a positive memory can help activate aspects of the brain that can cause the positive memory to be more mentally accessible and strengthen the calming centers of the brain. Visualization can also be powerful in these processes in that the same neurons within the visual cortex fire whether an event is actually happening or we are simply imagining it happening. As such, it can be possible to build mental retreats simply by imagining them.

With this in mind, tactile bilateral stimulation with an interim pause can be beneficial in the brain rewiring process for a number of reasons. For example, in some cases, bilateral stimulation can enhance mental imagery. In some additional examples, bilateral stimulation can have a naturally calming effect. Furthermore, bilateral stimulation with an interim pause can help prompt the user to engage in specific brain rewiring techniques, including the following: (a) switching back and forth from a positive to a negative memory, (b) highlighting different features of a memory, including visual, audio, emotions, body sensations, and intentions associated with that memory, (c) enhancing mental imagery through visualization of different features of an imagined mental retreat (e.g. imagined sights, sounds, textures, emotions) associated with a particular visualization, (d) engaging in any other number of steps or stages associated with the brain rewiring programs associated with the device, the like, or a combination thereof. As such, the interim pause can provide the pacing and the direction of the brain rewiring process, and can go beyond simply providing a relaxed experience to one that can help change and enhance adaptive memory networks. Further, the interim pause can be automated via software programming to allow the user to stay engaged with the treatment module. In contrast, where an end user has to turn off the device to simulate the interim pause, the treatment module can be disrupted, the user can disengage from the treatment protocol, and the treatment benefits can be substantially diminished or compromised.

EXAMPLES

Example 1 Therapeutic Effect of Interim Pause

Multiple subjects were exposed to vibrational bilateral stimulations with and without an interim pause. It was observed that the majority of the subjects exposed to bilateral stimulations lost focus and concentration when the bilateral stimulations last for longer than 1.5-2 minutes without a break. It also appeared that the relaxation effect is reduced during prolonged bilateral stimulations (i.e. the bilateral stimulations seemed less relaxing when they are ongoing without a pause). While the specific physiological components related to this are not known, it is believed that without an interim pause, the bilateral stimulations are more like background noise or static, simply interrupting thought processes rather than helping to move them forward. Much like a run-on sentence without the appropriate punctuation, bilateral stimulations without an interim pause do not appear to provide enhanced clarity or thought organization, nor do they appear to help specific thoughts to be organized and stored away in long-term storage so that they are no longer taking up space in the working memory.

However, when an interim pause is included, bilateral stimulations appear to aid subjects in organizing and processing thoughts and memories, and storing them into long-term memory, thus freeing up space within working memory. In addition, bilateral stimulations with an interim pause appear to change the type of emotions that are stored with that memory, in essence decreasing the intensity of the emotions as they are processed and stored away. There are many benefits associated with processing information using this approach, including overall decreased distress related to the memory, increased ability to focus and concentrate on matters associated with the here and now, decreased tendency to ruminate on things about the past, etc.

Example 2 Vibrational Intensity of Various Devices

Figure 9A:
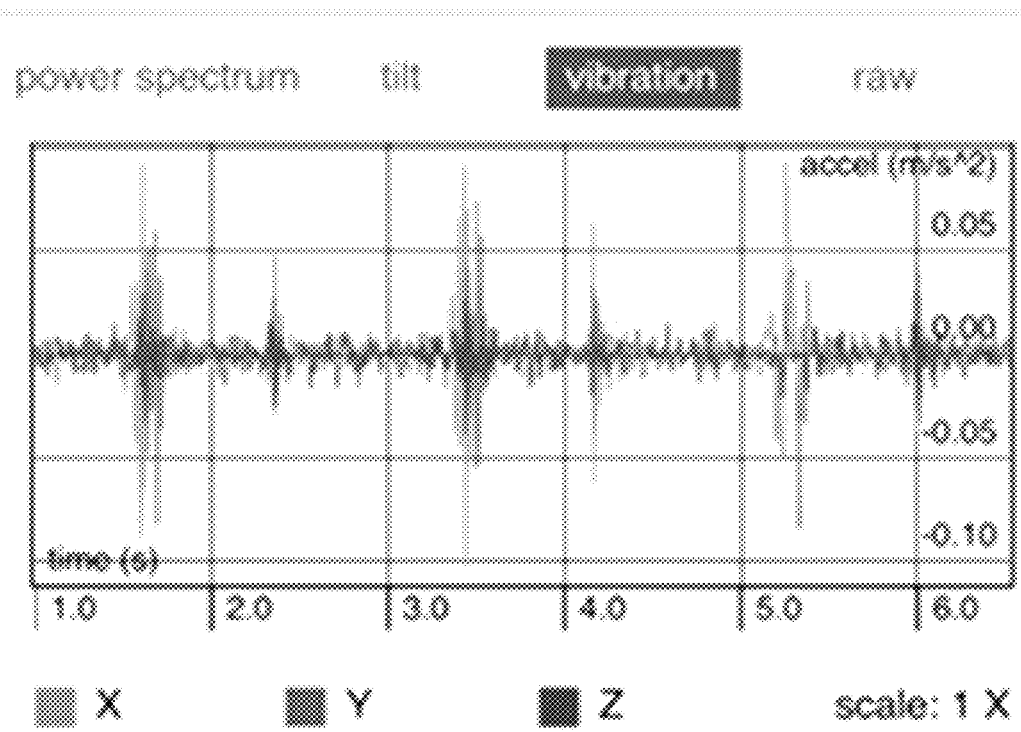
FIG. 9A is a graph of vibrational data generated from a first comparative vibrational device.
Figure 9B:
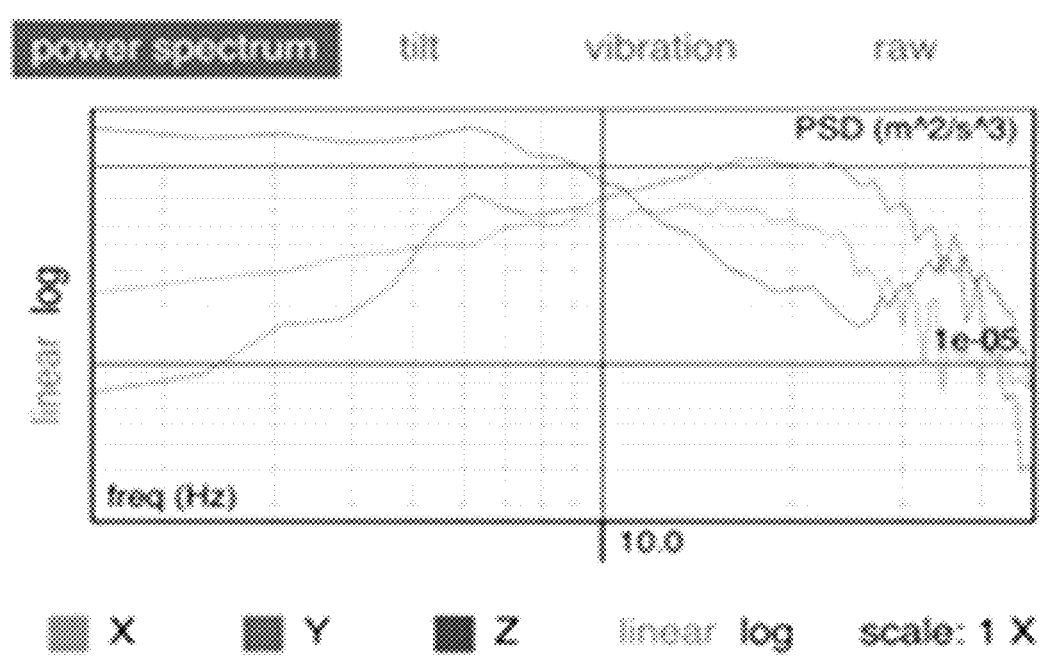
FIG. 9B is a graph of power spectrum data generated from the first comparative vibrational device.
Figure 10A:
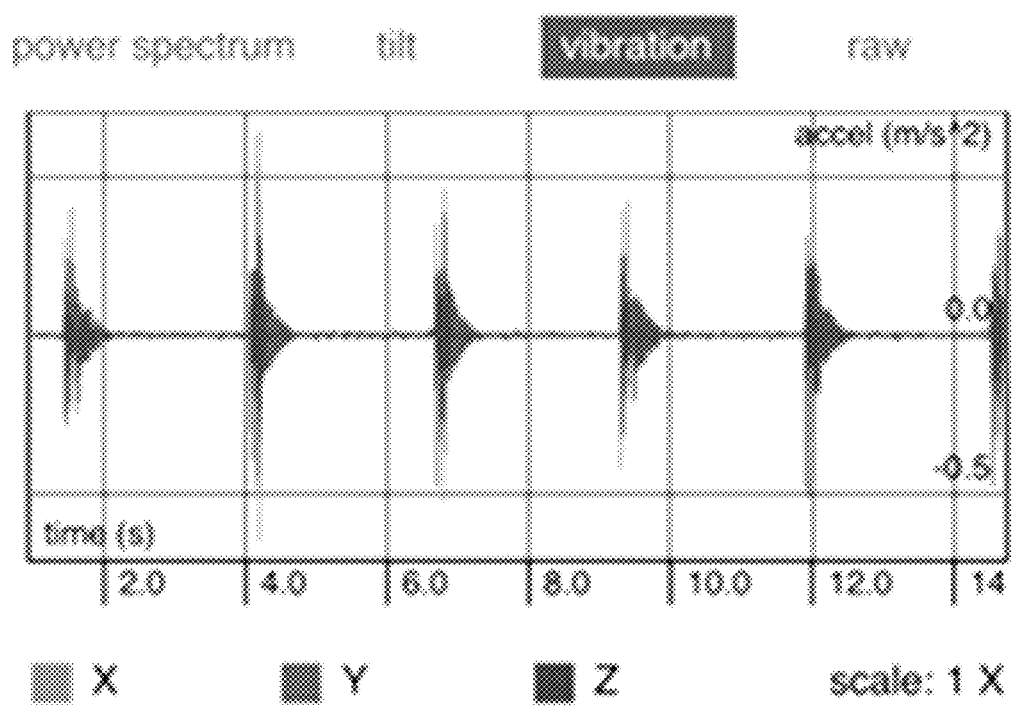
FIG. 10A is a graph of vibrational data generated from a second comparative vibrational device.
Figure 10B:
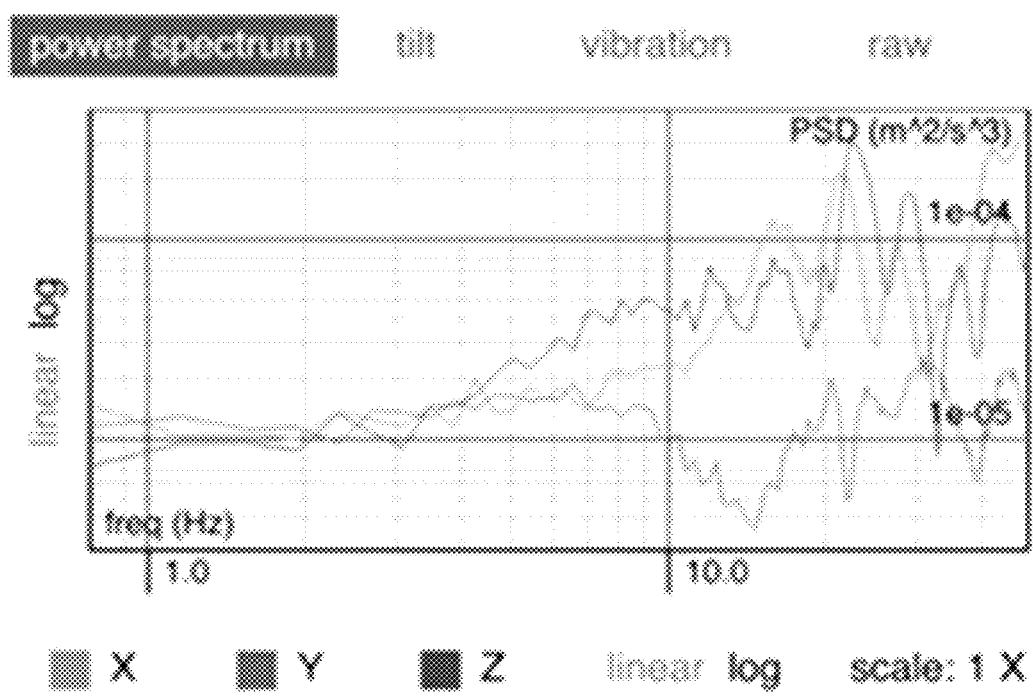
FIG. 10B is a graph of power spectrum data generated from the second comparative vibrational device.
Figure 11A:
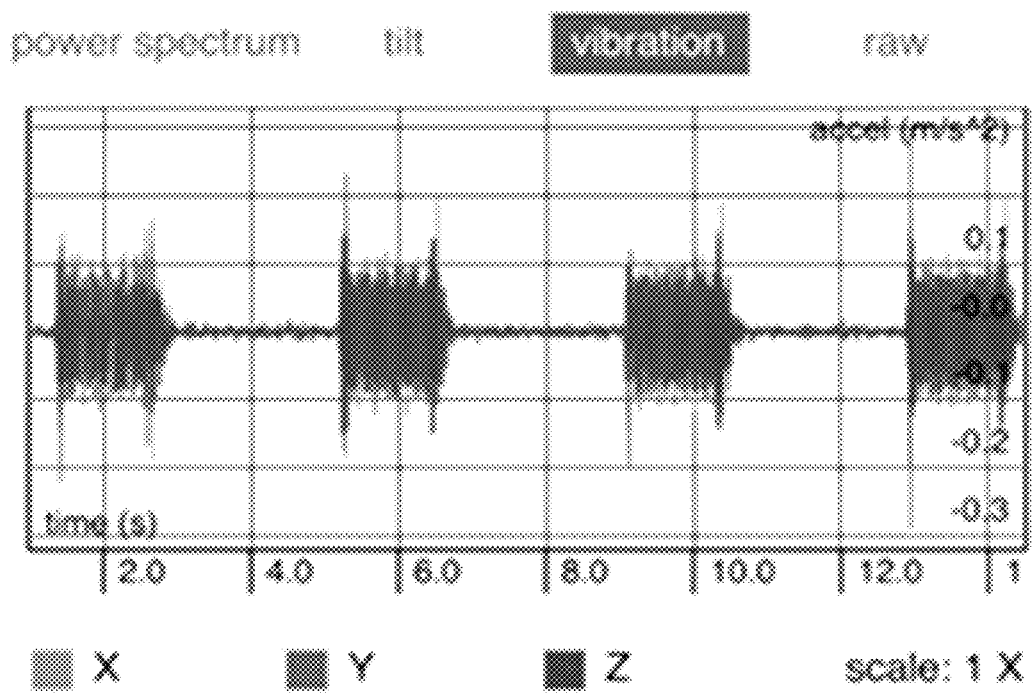
FIG. 11A is a graph of vibrational data generated from a BLS device, in accordance with examples of the present disclosure.
Figure 11B:
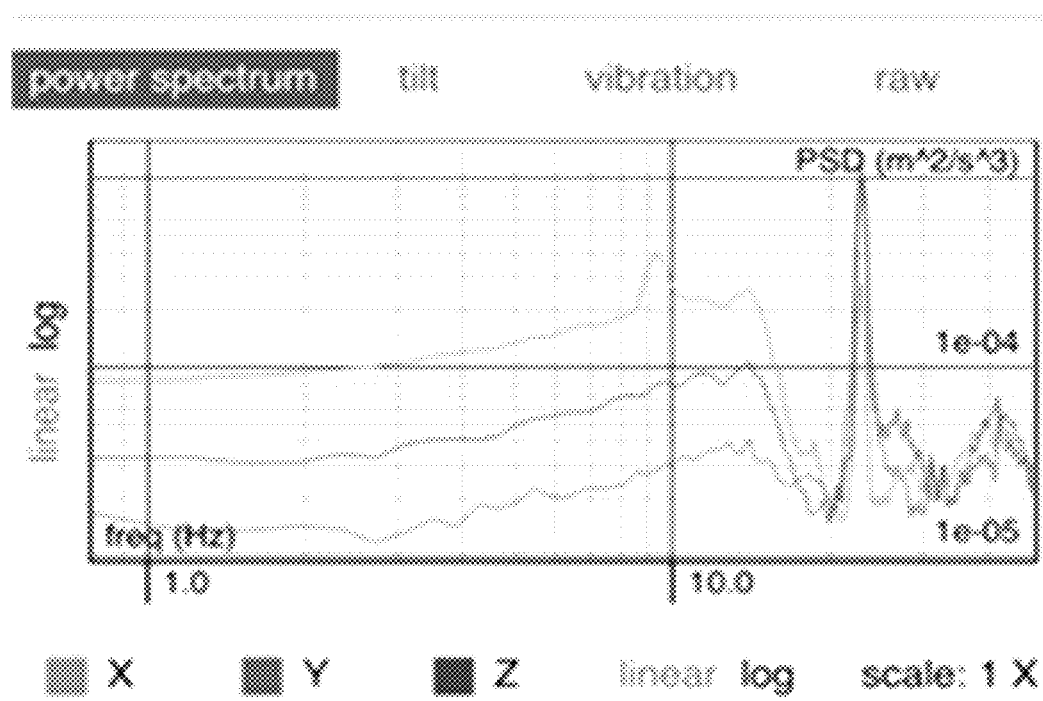
FIG. 11B is a graph of power spectrum data generated from a BLS device, in accordance with examples of the present disclosure.
Figure 12A:
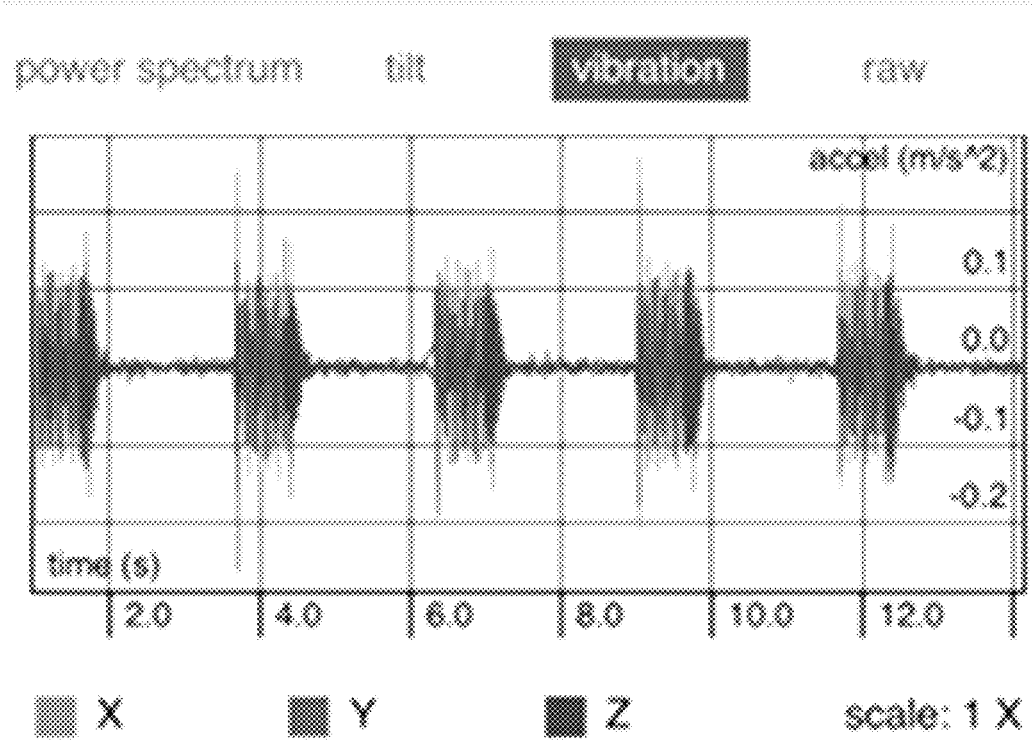
FIG. 12A is a graph of vibrational data generated from a BLS device, in accordance with examples of the present disclosure.
Figure 12B:
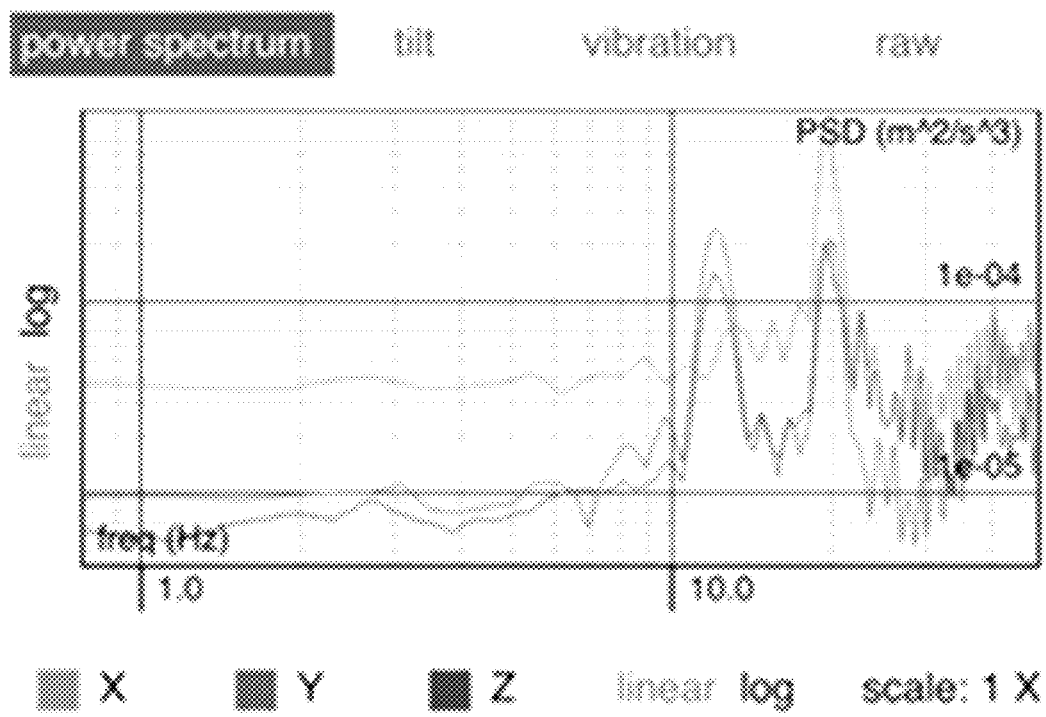
FIG. 12B is a graph of power spectrum data generated from a BLS device, in accordance with examples of the present disclosure.
Figure 13A:
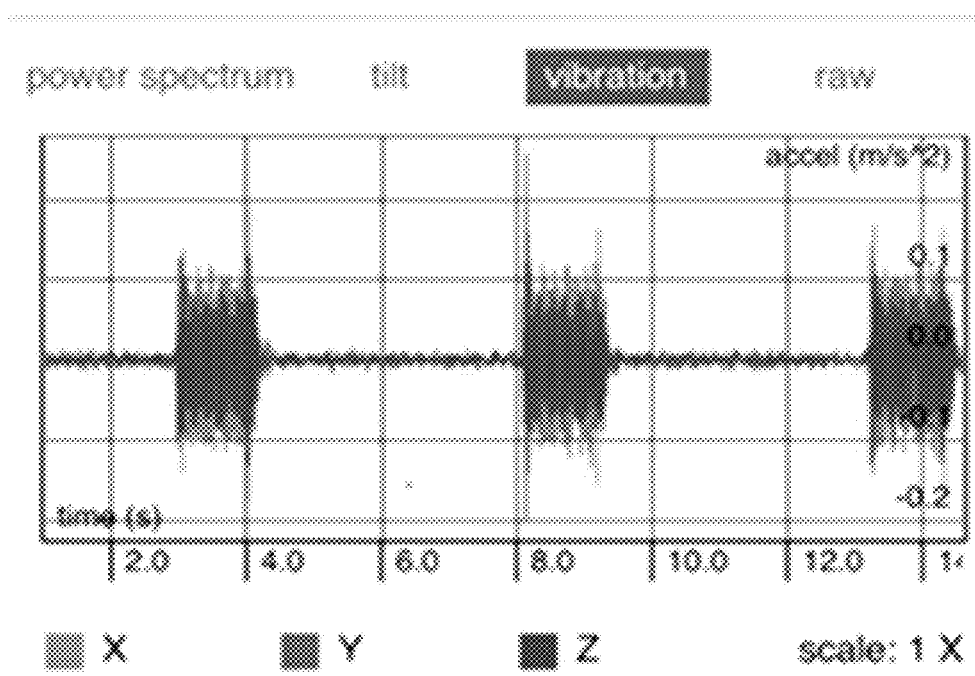
FIG. 13A is a graph of vibrational data generated from a BLS device, in accordance with examples of the present disclosure.
Figure 13B:
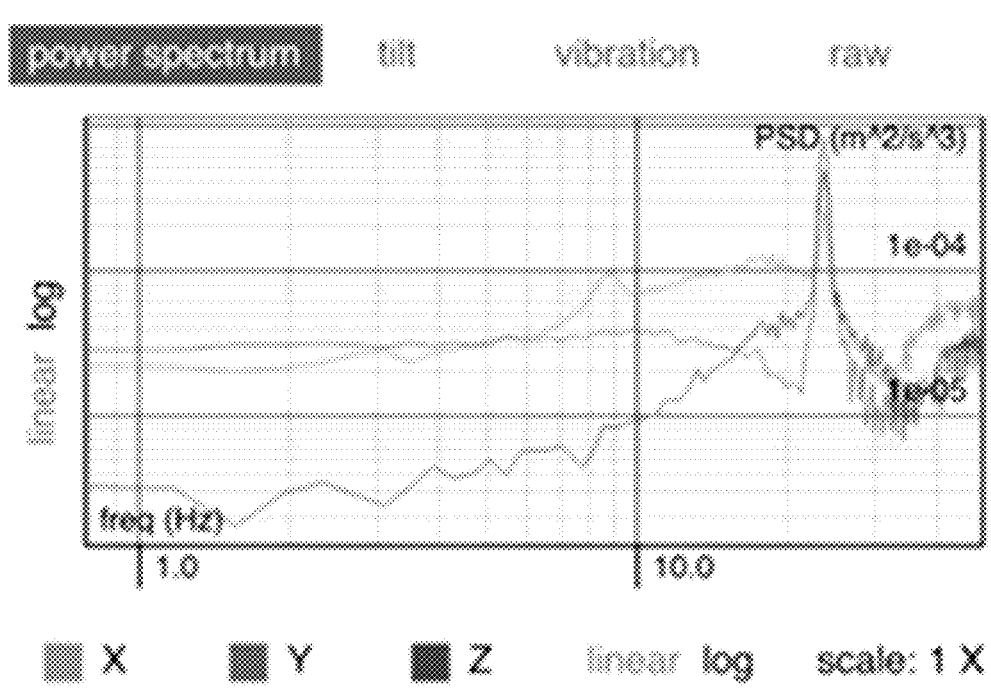
FIG. 13B is a graph of power spectrum data generated from a BLS device, in accordance with examples of the present disclosure.
Figure 14A:
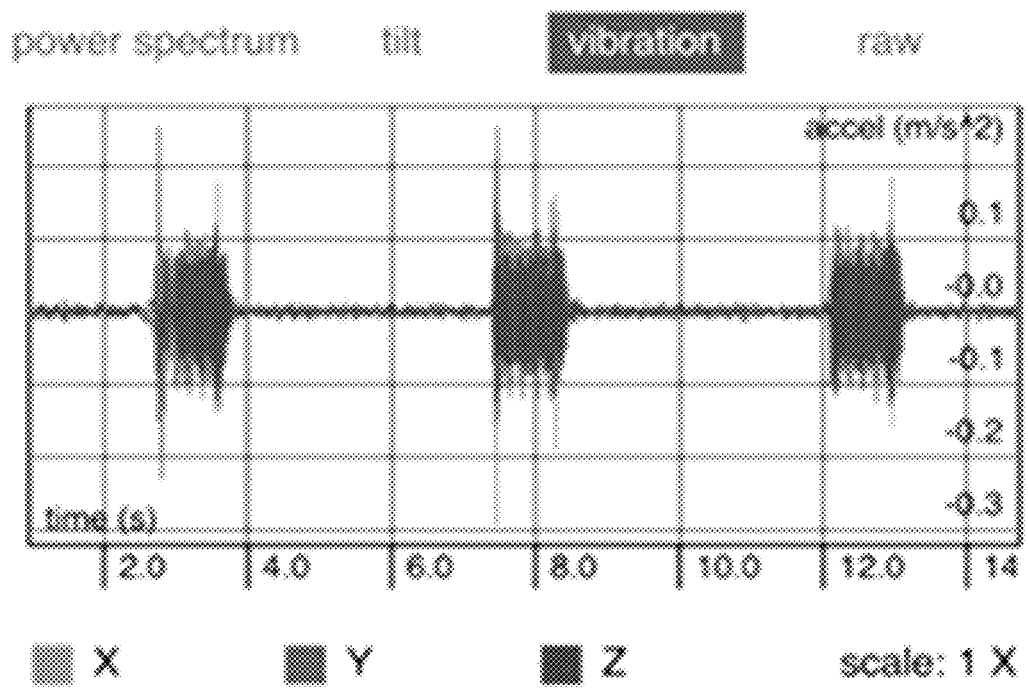
FIG. 14A is a graph of vibrational data generated from a BLS device, in accordance with examples of the present disclosure.
Figure 14B:
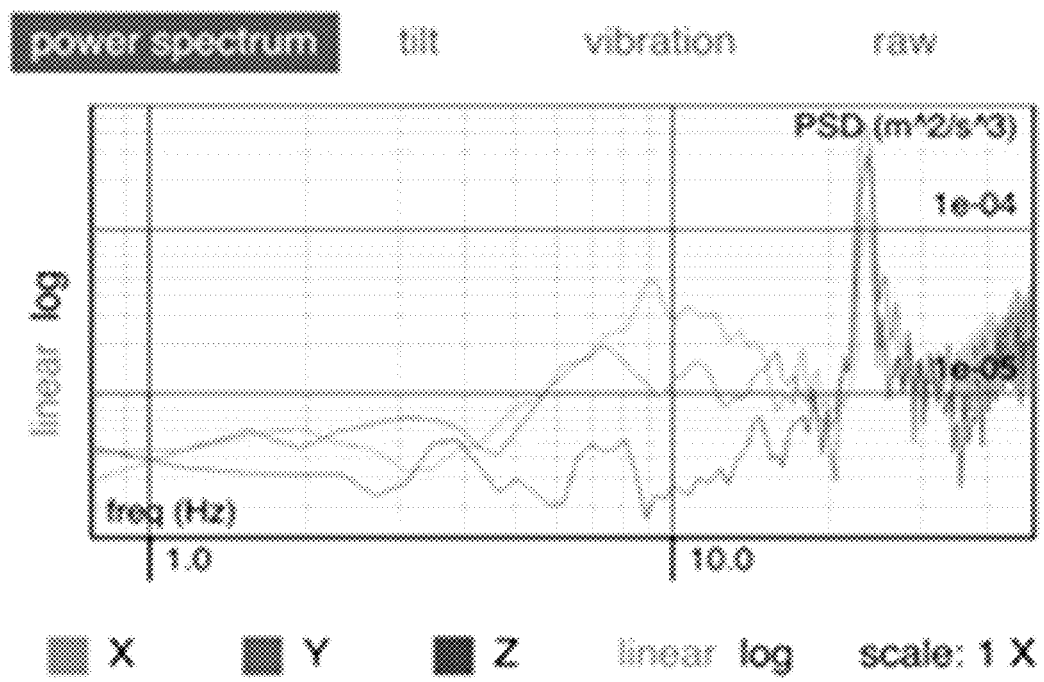
FIG. 14B is a graph of power spectrum data generated from a BLS device, in accordance with examples of the present disclosure.

A single BLS device as described herein was evaluated to collect vibrational and power spectrum (i.e. power vs. frequency) data for various treatment modality settings. The same types of data were also collected for two comparative products available on the market. The data for the first comparative product is presented in FIGS. 9A-9B. The data for the second comparative product is presented in FIGS. 10A-10B.

In further detail, the data sets presented in FIGS. 11A-11B, 12A-12B, 13A-13B, and 14A-14B are vibrational plot characterizations and spectrographs collected from one example BLS device employing four different vibrational programs, respectively. More specifically, the vibrational programs tested were targeted for addressing specific mental states of calm (FIGS. 11A-11B), tension (FIGS. 12A-12B), sleep (FIGS. 13A-13B), and meditation (14A-14B). The combination of intensity, duration, frequency, pause, and stimulation rate parameters are important for targeting the desired state of self-awareness, since each program is intended to address a particular stress tensor. The pulse programs employed in the BLS device are characteristically lower frequency, longer duration, smoother delivery and with a more generous pause as compared to the first and second comparative products.

Another particular differentiating feature is that the tested BLS device focuses the vibrational energy (noted by the strong ~25 Hz PDS peak in the power spectrum plots), except for the tension program, which is intentionally broader spectrum. The BLS device is intended to focus or concentrate the vibrational energy at lower frequencies (<75 Hz) by design rather than due to a hardware limitation.

It is believed that the bilateral stimulations from the present BLS device differentiates from the first and second comparative devices in that it has a different mechanism in terms of its effect on the brain. Specifically, while the first comparative products appear to create interruptive static in the brain that decreases the brains ability to activate the fight or flight response, the bilateral vibrations of the present BLS device may enhance the activation of the alpha (8-12 Hz) and theta (3-8 Hz) brain waves, which are believed to be associated with REM cycles, the intersection of the subconscious and conscious mind, and is associated with meditation and thereby enhance internal and external connection to the present. Alpha brain waves are associated with the resting state of the brain, allowing mental coordination, calmness, learning, and enhanced mind/body integration.

Turning now to FIG. 15, there is shown a process for automatically adjusting treatment (e.g. treatment parameters) according to an aspect of the present invention. As shown, treatment is initiated on a subject and biofeedback data is collected from the subject using biofeedback sensors. The biofeedback data is analyzed using a processor and a comparison can be made to an expected outcome or expected data. Expectations regarding outcome can be established either by an operator of the device, or by a data set or logic programmed into the device, or a device controller. In the latter case, a data set of points which represent biofeedback responses for a "normal" subject can be used. Further, a progressive data set that represents data collected from past usage, or extrapolated from past usage of the device by the subject can also be used. In this way, a subject's progress gained from using the device over time can be measured and long term therapeutic results can be pursued.

In another example, the process can comprise: initiating stimulation, collecting biofeedback data, analyzing biofeedback data using logic or software, such as AI software, and adjusting the stimulation using the AI software. The stimulation to be adjusted can include vibrational variables (e.g., frequency, intensity, speed, acceleration, duration, pause, patterns, sets of patterns, or the like). The stimulation adjustment can be adjusted based on a user input. The process can include real-time adjustments to the BLS variables based on the design of an experiment or a treatment modality.

EXAMPLE EMBODIMENTS

In one example there is provided, a bilateral stimulation (BLS) device, comprising a housing; a tactile stimulator coupled to the housing; a communications module configured to receive wireless communication from a remote device; and a controller module configured to independently and selectively control at least one tactile setting of the tactile stimulator based on wireless communication received from the remote device.

In one example of a BLS device, the housing further comprises an insulating material configured to reduce the detectability of audible vibrations.

In one example of a BLS device, the tactile stimulator comprises a piezoelectric device, an electromechanical actuator, an electromagnetic device, a disc vibration motor, an ultrasonic vibrator, or a combination thereof.

In one example of a BLS device, the tactile stimulator is configured to vibrate at a vibrational frequency of from about 5 hertz (Hz) to about 400 Hz.

In one example of a BLS device, the device further comprises a plurality of tactile stimulators.

In one example of a BLS device, the tactile stimulator is configured to have a decibel level at or below 35 at a distance of 0.5 meters (m) from the tactile stimulator.

In one example of a BLS device, the device further comprises a timer configured to terminate tactile stimulations of the tactile stimulator after expiration of a predetermined time limit.

In one example of a BLC device, the device further comprises a speaker, a screen, a microphone, or a combination thereof.

In one example of a BLS device, the device further comprises a receptacle for a fragrance.

In one example of a BLS device, the device further comprises a biofeedback sensor.

In one example of a BLS device, the communications module is configured to receive and transmit information wirelessly.

In one example of a BLS device, the at least one tactile setting comprises vibrational frequency, vibrational intensity, or a combination thereof.

In one example of a BLS device, the device further comprises a switch to control the at least one tactile setting without using the remote device.

In one example there is provided a bilateral stimulation (BLS) system, comprising a plurality of BLS devices according to claim 1 configured to wirelessly sync via a remote device.

In one example of a BLS system, the system further comprises a flexible article coupled one or more of the BLS devices.

In one example of a BLS system, the flexible article is coupled to each of the plurality of BLS devices.

In one example of a BLS system, the BLS system is a modular system.

In one example of a BLS system, the BLS system is a non-modular system.

In one example of a BLS system, the system further comprises a biofeedback sensor configured to wirelessly sync to the plurality of BLS devices via the remote device.

In one example of a BLS system, the biofeedback sensor is a heart rate monitor, a brain wave monitor, or a combination thereof.

In one example of a BLS system, the system further comprises a visual augmented reality (VAR) device configured to wirelessly sync to the plurality of BLS devices via the remote device.

In one example there is provided a method of treating an adverse health condition in a subject, comprising, either wiredly, or wirelessly connecting a plurality of BLS devices according to claim 1 via a remote device; based on instructions received from the remote device, applying a tactile stimulus to left and right sides of a subject body at a therapeutic frequency for a treatment period using the plurality of BLS devices; and based on instructions received from the remote device, performing an automated interim pause at least once during the treatment period for a duration of from about 5 seconds to about 5 minutes, wherein at least one tactile stimulus is applied after the interim pause.

In one example of a method of treating an adverse health condition, the tactile stimulus comprises a tactile pulse and a tactile pause.

In one example of a method of treating an adverse health condition, the tactile stimulus is applied in an alternating side-to-side pattern.

In one example of a method of treating an adverse health condition, the treatment period has a duration of from about 5 minutes to about 30 minutes.

In one example of a method of treating an adverse health condition, the remote device is a smart device.

In one example of a method of treating an adverse health condition, the smart device is configured to apply a tactile stimulus to the subject.

In one example of a method of treating an adverse health condition, the method further comprises collecting biofeedback information from the subject.

In one example of a method of treating an adverse health condition, the method further comprises adjusting the tactile stimulus, providing instructions, or a combination thereof based on biofeedback information received.

In one example of a method of treating an adverse health condition, further comprises providing audio information to the subject via a speaker.

In one example of a method of treating an adverse health condition, the audio information comprises instructions for the subject to follow, questions for the subject to answer, or a combination thereof.

In one example of a method of treating an adverse health condition, the method further comprises providing visual information to the subject via a display, glasses, a headset, or a combination thereof.

In one example of a method of treating an adverse health condition, the visual information comprises instructions for the subject to follow, questions for the subject to answer, or a combination thereof.

In one example of a method of treating an adverse health condition, the method further comprises: based on program logic of the remote device, administering one or more questions to the end user via communication transmitted from the remote device; receiving user input at the remote device in response to the one or more questions; and adjusting the tactile stimulus instructions transmitted from the remote device based on user input received.

In one example of a method of treating an adverse health condition, the communication transmitted from the remote device is an audio communication, a visual communication, or a combination thereof.

In one example of a method of treating an adverse health condition, user responses are provided to the remote device via audio communication, tactile data entry, or a combination thereof.

In one example of a method of treating an adverse health condition, the method further comprises providing a cognitive cue during the pause.

In one example of a method of treating an adverse health condition, wherein the cognitive cue is an affirmation or suggestion that provides thought-stimulating information to the subject.

In one example of a method of treating an adverse health condition, the information reminds the subject of a negative impact of stress on cognitive processes and triggers an awareness of the subject's negative memory networks and thinking patterns.

In one example of a method of treating an adverse health condition, the information reminds the subject to recall positive information.

In one example of a method of treating an adverse health condition, the cognitive cue is either visual or auditory.

In one example there is provided a method of enhancing a subject's ability to engage in dual simultaneous awareness and enhance the subject's ability to rewire or change memory networks in order to decrease stress, comprising: engaging a BLS device or system as recited herein; operating the BLS device or system to create an experience of calm and allow the subject to engage specific features of a selected memory; pausing BLS; and prompting the subject to cognitively modify the memory to enhance positive features and neutralize negative features of an associated memory network.

In one example of a method of enhancing a subject's ability to engage in dual simultaneous awareness, the prompting includes providing cognitive cues of specific mental activities that enhance an ability to use dual simultaneous awareness to enhance specific of memory networks.

In one example of a method of enhancing a subject's ability to engage in dual simultaneous awareness, the enhancement is to either neutralizes negative memory networks or enhances positive memory networks, or both.

In one example of a method of enhancing a subject's ability to engage in dual simultaneous awareness, the BLS provides a level of calm which facilitates engaging in productive simultaneous dual awareness for effective changing of memory networks.

In one example of a method of enhancing a subject's ability to engage in dual simultaneous awareness, wherein the pausing creates a sense of pacing and a point of reference for the mental activities associated with changing a memory network.

In one example, a bilateral stimulation (BLS) system can comprise a plurality of devices. The BLS system can comprise a first device comprising: a first tactile stimulator, and a first communications module configured to communicate with a second device. The second device can comprise a second tactile stimulator; and a second communications module configured to communicate with the first device. The BLS system can comprise a controller module including logic configured to control operation of the first and second tactile stimulators to induce tactile events according to a BLS program. In one example, operation of the first and second tactile stimulators can include at least one pause for a selected duration between tactile events in the BLS program.

In one example, the first device or the second device can be located in separate housing or shared housing. In one example, the housing can further include an insulating material configured to reduce the detectability of audible vibrations.

In one example, the first and second tactile stimulators can comprise a piezoelectric device, an electromechanical actuator, an electromagnetic device, a disc vibration motor, an ultrasonic vibrator, inertia pulse generator, inductive voltage stimulation, heat sink, cold sink, or a combination thereof.

In one example, the first and second tactile stimulators can be configured to vibrate at a vibrational frequency selected to treat an adverse health condition.

In one example, the first and second tactile stimulators can be configured to have a decibel level at or below 35 at a distance of 0.5 meters (m) from the tactile stimulator.

In one example, the controller module can further comprise a timer configured to terminate tactile stimulations of the tactile stimulator after expiration of a predetermined time limit.

In one example, the first or second devices can further comprise a speaker, a microphone, or both.

In one example, the BLS system can further comprise a receptacle for a fragrance.

In one example, the BLS system can further comprise a biofeedback sensor.

In one example, the first and second communication modules can be configured to communicate information wirelessly.

In one example, the BLS program can comprise vibrational frequency, vibrational intensity, vibrational speed, vibrational acceleration, vibrational duration, vibrational pause, vibrational patterns, sets of vibrational patterns, or a combination thereof.

In one example, the first or second device can further comprise a switch to control the at least one BLS program without using the controller module.

In one example, the BLS system can further comprise a flexible article coupled to the first or second device. In one example, the flexible article can be coupled to each of the first device and the second device.

In one example, either the first or second device can include the controller module.

In one example, either the first device, the second device, or both the first device and the second device can be a smart device.

In one example, the BLS system can further comprise a remote device including the controller module.

In one example, the BLS system can be a modular system configured to vibrate at resonant frequencies.

In one example, the BLS system can further comprise a single integrated device.

In one example, the BLS system can further comprise a biofeedback sensor configured to communicate with the controller module. In one example, the biofeedback sensor can be a heart rate sensor, a brain wave sensor, a perspiration sensor, a muscle tension sensor, a nerve conduction sensor, an optical sensor, or a combination thereof.

In one example, the BLS system can further comprise a visual augmented reality (VAR) device configured to communicate with the controller module.

In one example, a method of treating an adverse health condition in a subject, can comprise providing a system as in the preceding, and operating the system on a subject.

In one example, the method can comprise providing an audio or visual cue to a subject to elicit feedback using one or more of an icon, a graphic, an image, a word, a phrase, an infographic, a situation, a story, a tone, a color, a shape, a diagram, an animation, an audio clip, a video display, or combinations thereof.

In one example, the adverse health condition can be selected from the group consisting of: post-traumatic stress disorder (PTSD), social anxiety, separation anxiety, generalized anxiety, panic, depression, relational conflict, phobias, traumatic experiences, chronic-pain induced stress, blended family conflict, marital conflict, relational attachment patterns, spectrum disorders, attention deficit hyperactivity disorder (ADHD), anger management, process addictions, eating disorders perfectionism, performance anxiety, parenting concerns, academic-focus difficulties, substance abuse, substance addiction, somatic stress, sleep disorders, and combinations thereof.

Various techniques, or certain aspects or portions thereof, may take the form of program code (i.e., instructions) embodied in tangible media, such as floppy diskettes, compact disc-read-only memory (CD-ROMs), hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a random-access memory (RAM), erasable programmable read only memory (EPROM), flash drive, optical drive, magnetic hard drive, solid state drive, or other medium for storing electronic data. The node and wireless device may also include a transceiver module (i.e., transceiver), a counter module (i.e., counter), a processing module (i.e., processor), and/or a clock module (i.e., clock) or timer module (i.e., timer). In one example, selected components of the transceiver module can be located in a cloud radio access network (C-RAN). One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

As used herein, the term "circuitry" may refer to, be part of, or include an Application Specific Integrated Circuit (ASIC), an electronic circuit, a processor (shared, dedicated, or group), and/or memory (shared, dedicated, or group) that execute one or more software or firmware programs, a combinational logic circuit, and/or other suitable hardware components that provide the described functionality. In some embodiments, the circuitry may be implemented in, or functions associated with the circuitry may be implemented by, one or more software or firmware modules. In some embodiments, circuitry may include logic, at least partially operable in hardware.

It should be understood that many of the functional units described in this specification have been labeled as modules, in order to more particularly emphasize their implementation independence. For example, a module may be implemented as a hardware circuit comprising custom very-large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module may not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Furthermore, the described features, structures, or characteristics may be combined in any suitable manner in one or more embodiments. In the following description, numerous specific details are provided, such as examples of layouts, distances, network examples, etc., to provide a thorough understanding of embodiments of the technology. One skilled in the relevant art will recognize, however, that the technology can be practiced without one or more of the specific details, or with other methods, components, layouts, etc. In other instances, well-known structures, materials, or operations are not shown or described in detail to avoid obscuring aspects of the technology.

While the forgoing examples are illustrative of the specific embodiments in one or more particular applications, it will be apparent to those of ordinary skill in the art that numerous modifications in form, usage and details of implementation can be made without departing from the principles and concepts articulated herein. Accordingly, no limitation is intended except as by the claims set forth below.

What is claimed is:

1. A bilateral stimulation (BLS) system, comprising a plurality of devices, including:
   a first device comprising:
   a first tactile stimulator; and
   a first communications module;
   a second device comprising:
   a second tactile stimulator; and
   a second communications module;
   a controller module configured to communicate with the first and the second communications modules and including logic configured to control operation of the first and second tactile stimulators to induce vibration events according to a BLS program, wherein operation of the first and second tactile stimulators includes at least one pause in vibration for a selected duration between vibration events in the BLS program; wherein either:
   the first device or the second device are located in a separate housing or shared housing, said housing further including an insulating material configured to reduce the detectability of audible vibration at a distance of 0.5 meters (m) from the first and second tactile stimulators; or
   the first and second tactile stimulators are configured to have a decibel level at or below 35 at a distance of 0.5 meters (m) from the first and second tactile stimulators.

2. The BLS system of claim 1, wherein the first and second tactile stimulators comprise a piezoelectric device, an electromechanical actuator, an electromagnetic device, a disc vibration motor, an ultrasonic vibrator, inertia pulse generator, inductive voltage stimulation, heat sink, cold sink, or a combination thereof.

3. The BLS system of claim 1, wherein the first and second tactile stimulators are configured to vibrate at a vibrational frequency selected to treat an adverse health condition.

4. The BLS system of claim 1, wherein the controller module further comprises a timer configured to terminate tactile stimulations of the first and second tactile stimulators after expiration of a predetermined time limit.

5. The BLS system of claim 1, wherein the first or second devices further comprises a speaker, a microphone, or both.

6. The BLS system of claim 1, further comprising a receptacle for a fragrance.

7. The BLS system of claim 1, further comprising a biofeedback sensor.

8. The BLS system of claim 1, wherein the first and second communication modules are configured to communicate information wirelessly.

9. The BLS system of claim 1, wherein the at least one BLS program comprises vibrational frequency, vibrational intensity, vibrational speed, vibrational acceleration, vibrational duration, vibrational pause, vibrational patterns, sets of vibrational patterns, or a combination thereof.

10. The BLS system of claim 1, wherein the first or second device further comprises a switch to control the at least one BLS program without using the controller module.

11. The BLS system of claim 1, further comprising a flexible article coupled to the first or second device.

12. The BLS system of claim 11, wherein the flexible article is coupled to each of the first device and the second device.

13. The BLS system of claim 1, wherein either the first or second device includes the controller module.

14. The BLS system of claim 1, wherein either the first device, the second device, or both the first device and the second device is a smart device.

15. The BLS system of claim 1, further comprising a remote device including the controller module.

16. The BLS system of claim 1, wherein the BLS system is a modular system.

17. The BLS system of claim 1, wherein the BLS system comprises a single integrated device.

18. The BLS system of claim 1, further comprising a biofeedback sensor configured to communicate with the controller module.

19. The BLS system of claim 18, wherein the biofeedback sensor is a heart rate sensor, a brain wave sensor, a perspiration sensor, a muscle tension sensor, a nerve conduction sensor, an optical sensor, or a combination thereof.

20. The BLS system of claim 1, further comprising a visual augmented reality (VAR) device configured to communicate with the controller module.

* * * * *